United States Patent
Marnay et al.

(10) Patent No.: US 8,349,017 B2
(45) Date of Patent: *Jan. 8, 2013

(54) INSTRUMENTS AND METHOD FOR INSERTING AN INTERVERTEBRAL IMPLANT

(75) Inventors: Theirry Marnay, Casteinau le Lez (FR); Rudolf Bertagnoli, Vienna (AT); Frank Magee, Ketchum, ID (US); Stephan Eckhof, Tuttlingen (DE); David L. Nichols, West Chester, PA (US); Christophe Geisert, Tuttlingen (DE)

(73) Assignee: Spine Solutions, Inc., West Chester, PA (US)

( * ) Notice: Subject to any disclaimer, the term of this patent is extended or adjusted under 35 U.S.C. 154(b) by 96 days.

This patent is subject to a terminal disclaimer.

(21) Appl. No.: 12/878,101

(22) Filed: Sep. 9, 2010

(65) Prior Publication Data
US 2010/0331988 A1    Dec. 30, 2010

Related U.S. Application Data

(62) Division of application No. 10/622,535, filed on Jul. 21, 2003, now Pat. No. 7,803,162.

(51) Int. Cl.
*A61F 2/44* (2006.01)
*A61B 17/56* (2006.01)

(52) U.S. Cl. ............... 623/17.16; 606/86 A; 606/99
(58) Field of Classification Search .... 623/17.11–17.16; 606/86 A, 99
See application file for complete search history.

(56) References Cited

U.S. PATENT DOCUMENTS

| | | | |
|---|---|---|---|
| 114,816 A | 5/1871 | Hiestand | |
| 3,320,951 A | 5/1967 | Wittebol | |
| 3,486,505 A * | 12/1969 | Morrison | 606/90 |
| 3,510,883 A | 5/1970 | Cathcart | |
| 3,579,829 A | 5/1971 | Sampson | |
| 3,740,769 A | 6/1973 | Haboush | |
| 3,875,595 A | 4/1975 | Froning | |
| 3,903,549 A | 9/1975 | Deyerle | |
| D243,286 S | 2/1977 | Deyerle | |
| 4,021,864 A | 5/1977 | Waugh | |
| 4,034,746 A | 7/1977 | Williams | |
| 4,038,897 A | 8/1977 | Murray et al. | |
| 4,038,987 A | 8/1977 | Komiya | |
| 4,232,404 A | 11/1980 | Samuelson et al. | |
| 4,309,777 A | 1/1982 | Patil | |

(Continued)

FOREIGN PATENT DOCUMENTS

CH    624 573    8/1981

(Continued)

OTHER PUBLICATIONS

English abstract of cited reference, DE 2804936 A1 corresponding to CH 624573, Aug. 1981, 1 page.

(Continued)

*Primary Examiner* — Pedro Philogene
(74) *Attorney, Agent, or Firm* — Woodcock Washburn LLP

(57) ABSTRACT

Instruments and methods for inserting an intervertebral implant. Insertion of the implant is accomplished by grasping the implant between the arms of an insertion instrument having arms which separate from each other and close against each other onto the implant, such that the ends of the arms of the insertion instrument engage recesses of the implant. A spacer may be provided between the arms of the insertion instrument to help position the implant while held by the arms.

25 Claims, 19 Drawing Sheets

U.S. PATENT DOCUMENTS

| | | | |
|---|---|---|---|
| 4,349,921 A | 9/1982 | Kuntz | |
| 4,467,802 A | 8/1984 | Maslanka | |
| 4,470,158 A | 9/1984 | Pappas et al. | |
| 4,545,374 A | 10/1985 | Jacobson | |
| 4,550,450 A | 11/1985 | Kinnett | |
| 4,622,959 A | 11/1986 | Marcus | |
| 4,653,487 A | 3/1987 | Maale | |
| 4,681,589 A | 7/1987 | Tronzo | |
| 4,697,586 A | 10/1987 | Gazale | |
| 4,714,469 A | 12/1987 | Kenna | |
| 4,736,738 A | 4/1988 | Lipovsek et al. | |
| 4,743,262 A | 5/1988 | Tronzo | |
| 4,759,766 A | 7/1988 | Buttner-Janz et al. | |
| 4,759,769 A | 7/1988 | Hedman et al. | |
| 4,770,661 A | 9/1988 | Oh | |
| 4,805,607 A | 2/1989 | Engelhardt et al. | |
| 4,863,476 A | 9/1989 | Shepperd | |
| 4,874,389 A | 10/1989 | Downey | |
| 4,875,474 A | 10/1989 | Border | |
| 4,892,545 A | 1/1990 | Day et al. | |
| 4,898,161 A | 2/1990 | Grundei | |
| 4,932,975 A | 6/1990 | Main et al. | |
| 4,936,863 A | 6/1990 | Hofmann | |
| 4,946,378 A | 8/1990 | Hirayama et al. | |
| 4,997,432 A | 3/1991 | Keller | |
| 5,002,576 A | 3/1991 | Fuhrmann et al. | |
| 5,004,476 A | 4/1991 | Cook | |
| 5,035,716 A | 7/1991 | Downey | |
| 5,037,438 A | 8/1991 | Davidson | |
| 5,062,850 A | 11/1991 | MacMillan et al. | |
| 5,071,437 A | 12/1991 | Steffee | |
| 5,108,442 A | 4/1992 | Smith | |
| 5,122,130 A | 6/1992 | Keller | |
| 5,171,280 A | 12/1992 | Baumgartner | |
| 5,192,327 A | 3/1993 | Brantigan | |
| 5,211,645 A | 5/1993 | Baumgartner et al. | |
| 5,228,455 A | 7/1993 | Barcel | |
| 5,236,460 A | 8/1993 | Barber | |
| 5,258,031 A | 11/1993 | Salib et al. | |
| 5,271,737 A | 12/1993 | Baldwin et al. | |
| 5,282,868 A | 2/1994 | Bahler | |
| 5,290,312 A | 3/1994 | Kojimoto et al. | |
| 5,306,308 A | 4/1994 | Gross et al. | |
| 5,306,309 A | 4/1994 | Wagner et al. | |
| 5,314,477 A | 5/1994 | Marnay | |
| 5,326,366 A | 7/1994 | Pascarella et al. | |
| 5,336,232 A | 8/1994 | Green et al. | |
| 5,344,458 A | 9/1994 | Bonutti | |
| 5,364,397 A | 11/1994 | Hayes et al. | |
| 5,370,697 A | 12/1994 | Baumgartner | |
| 5,383,888 A | 1/1995 | Zvenyatsky et al. | |
| 5,395,317 A | 3/1995 | Kambin | |
| 5,401,269 A | 3/1995 | Buttner-Janz et al. | |
| 5,409,492 A | 4/1995 | Jones et al. | |
| 5,423,825 A | 6/1995 | Levine | |
| 5,425,773 A | 6/1995 | Boyd et al. | |
| 5,431,658 A * | 7/1995 | Moskovich | 606/99 |
| 5,443,514 A | 8/1995 | Steffee | |
| 5,458,641 A | 10/1995 | Ramirez Jimenez | |
| 5,484,437 A | 1/1996 | Michelson | |
| 5,489,307 A | 2/1996 | Kuslich et al. | |
| 5,501,654 A | 3/1996 | Failla et al. | |
| 5,505,732 A | 4/1996 | Michelson | |
| 5,507,816 A | 4/1996 | Bullivant | |
| 5,509,934 A | 4/1996 | Cohen | |
| 5,534,029 A | 7/1996 | Shima | |
| 5,534,030 A | 7/1996 | Navarro et al. | |
| 5,554,191 A | 9/1996 | Lahille et al. | |
| 5,556,431 A | 9/1996 | Buttner-Janz et al. | |
| 5,562,736 A | 10/1996 | Ray et al. | |
| 5,562,738 A | 10/1996 | Boyd et al. | |
| 5,571,109 A | 11/1996 | Bertagnoli | |
| 5,591,235 A | 1/1997 | Kuslich | |
| 5,609,636 A | 3/1997 | Kohrs et al. | |
| 5,658,347 A | 8/1997 | Sarkisian et al. | |
| 5,676,701 A | 10/1997 | Yuan et al. | |
| 5,683,465 A | 11/1997 | Shinn et al. | |
| 5,702,469 A | 12/1997 | Whipple et al. | |
| 5,702,486 A | 12/1997 | Craig et al. | |
| 5,716,415 A | 2/1998 | Steffee | |
| 5,720,751 A * | 2/1998 | Jackson | 606/86 R |
| 5,722,977 A | 3/1998 | Wilhelmy | |
| 5,755,811 A | 5/1998 | Tanamal et al. | |
| 5,776,199 A | 7/1998 | Michelson | |
| 5,782,830 A | 7/1998 | Farris | |
| 5,782,832 A | 7/1998 | Larsen et al. | |
| 5,797,909 A | 8/1998 | Michelson | |
| 5,800,547 A | 9/1998 | Schafer et al. | |
| 5,824,094 A | 10/1998 | Serhan et al. | |
| D401,335 S | 11/1998 | Koros et al. | |
| 5,865,848 A | 2/1999 | Baker | |
| 5,885,300 A | 3/1999 | Tokuhashi et al. | |
| 5,888,226 A | 3/1999 | Rogozinski | |
| 5,895,428 A | 4/1999 | Berry | |
| 5,897,593 A | 4/1999 | Kohrs et al. | |
| 5,899,901 A | 5/1999 | Middleton | |
| 5,899,941 A | 5/1999 | Nishijima et al. | |
| 5,951,564 A | 9/1999 | Schroder et al. | |
| 6,006,174 A | 12/1999 | Lin et al. | |
| 6,010,502 A | 1/2000 | Bagby | |
| 6,017,342 A * | 1/2000 | Rinner | 606/57 |
| 6,033,405 A | 3/2000 | Winslow et al. | |
| 6,036,692 A | 3/2000 | Burel et al. | |
| 6,042,582 A | 3/2000 | Ray | |
| 6,059,790 A | 5/2000 | Sand et al. | |
| 6,063,088 A | 5/2000 | Winslow | |
| 6,063,121 A | 5/2000 | Xavier et al. | |
| 6,080,155 A | 6/2000 | Michelson | |
| 6,083,225 A | 7/2000 | Winslow et al. | |
| 6,086,595 A | 7/2000 | Yonemura et al. | |
| 6,096,038 A | 8/2000 | Michelson | |
| 6,096,080 A | 8/2000 | Nicholson et al. | |
| 6,102,950 A | 8/2000 | Vaccaro | |
| 6,102,954 A | 8/2000 | Albrektsson et al. | |
| 6,110,179 A | 8/2000 | Flivik et al. | |
| 6,113,602 A | 9/2000 | Sand | |
| 6,113,637 A | 9/2000 | Gill et al. | |
| 6,113,638 A | 9/2000 | Williams et al. | |
| 6,117,174 A | 9/2000 | Nolan | |
| 6,126,660 A | 10/2000 | Dietz | |
| 6,126,674 A | 10/2000 | Janzen | |
| 6,146,421 A | 11/2000 | Gordon et al. | |
| 6,156,040 A | 12/2000 | Yonemura et al. | |
| 6,159,215 A | 12/2000 | Urbahns et al. | |
| 6,171,339 B1 | 1/2001 | Houfburg et al. | |
| 6,174,311 B1 | 1/2001 | Branch et al. | |
| 6,224,599 B1 | 5/2001 | Baynham et al. | |
| 6,238,414 B1 | 5/2001 | Griffiths | |
| 6,241,769 B1 | 6/2001 | Nicholson et al. | |
| 6,251,140 B1 | 6/2001 | Marino et al. | |
| 6,261,296 B1 | 7/2001 | Aebi et al. | |
| 6,264,655 B1 | 7/2001 | Pisharodi | |
| 6,270,498 B1 | 8/2001 | Michelson | |
| 6,296,647 B1 | 10/2001 | Robioneck et al. | |
| 6,309,421 B1 | 10/2001 | Pisharodi | |
| 6,368,350 B1 | 4/2002 | Erickson et al. | |
| 6,368,351 B1 | 4/2002 | Glenn et al. | |
| 6,375,681 B1 | 4/2002 | Truscott | |
| 6,402,785 B1 | 6/2002 | Zdeblick et al. | |
| 6,413,278 B1 | 7/2002 | Marchosky | |
| 6,436,139 B1 | 8/2002 | Shapiro et al. | |
| 6,440,142 B1 | 8/2002 | Ralph et al. | |
| 6,440,168 B1 | 8/2002 | Cauthen | |
| 6,440,169 B1 * | 8/2002 | Elberg et al. | 623/17.16 |
| 6,447,547 B1 | 9/2002 | Michelson | |
| 6,478,800 B1 | 11/2002 | Fraser et al. | |
| 6,478,801 B1 | 11/2002 | Ralph et al. | |
| 6,478,823 B1 | 11/2002 | Michelson | |
| 6,500,206 B1 | 12/2002 | Bryan | |
| 6,517,544 B1 | 2/2003 | Michelson | |
| 6,558,424 B2 | 5/2003 | Thalgott | |
| 6,565,574 B2 | 5/2003 | Michelson | |
| 6,595,995 B2 | 7/2003 | Zdeblick et al. | |
| 6,599,294 B2 | 7/2003 | Fuss et al. | |
| 6,610,065 B1 | 8/2003 | Branch et al. | |
| 6,613,091 B1 | 9/2003 | Zdeblick et al. | |
| 6,635,060 B2 | 10/2003 | Hanson et al. | |

| | | | |
|---|---|---|---|
| 6,641,582 B1 | 11/2003 | Hanson et al. | |
| 6,641,614 B1 | 11/2003 | Wagner et al. | |
| 6,652,533 B2 | 11/2003 | O'Neil | |
| 6,652,534 B2 | 11/2003 | Zucherman et al. | |
| 6,712,819 B2 | 3/2004 | Zucherman et al. | |
| 6,712,825 B2 | 3/2004 | Aebi et al. | |
| 6,733,505 B2 | 5/2004 | Li | |
| 6,740,118 B2 | 5/2004 | Eisermann | |
| 6,746,454 B2 | 6/2004 | Winterbottom et al. | |
| 6,755,841 B2 | 6/2004 | Fraser et al. | |
| 6,770,074 B2 | 8/2004 | Michelson | |
| 6,824,565 B2 | 11/2004 | Muhanna et al. | |
| 6,875,213 B2 | 4/2005 | Michelson | |
| 6,896,676 B2 | 5/2005 | Zubok et al. | |
| 6,936,071 B1 | 8/2005 | Marnay et al. | |
| 6,964,687 B1 | 11/2005 | Bernard et al. | |
| 6,966,912 B2 | 11/2005 | Michelson | |
| 7,081,120 B2 | 7/2006 | Li et al. | |
| 7,118,580 B1 | 10/2006 | Beyersdorff et al. | |
| 7,169,182 B2 | 1/2007 | Errico et al. | |
| 7,204,852 B2 * | 4/2007 | Marnay et al. | 623/17.16 |
| 7,238,203 B2 | 7/2007 | Bagga et al. | |
| 7,252,673 B2 | 8/2007 | Lim | |
| 7,491,204 B2 | 2/2009 | Marnay | |
| 7,547,309 B2 | 6/2009 | Bertagnoli et al. | |
| 7,575,576 B2 | 8/2009 | Zubok et al. | |
| 7,803,162 B2 * | 9/2010 | Marnay et al. | 606/99 |
| 8,025,684 B2 * | 9/2011 | Garcia-Bengochea et al. | 606/279 |
| 2002/0016633 A1 | 2/2002 | Lin et al. | |
| 2002/0049497 A1 | 4/2002 | Mason | |
| 2002/0072752 A1 | 6/2002 | Zucherman et al. | |
| 2002/0077702 A1 | 6/2002 | Castro | |
| 2002/0165612 A1 | 11/2002 | Gerber et al. | |
| 2003/0069586 A1 | 4/2003 | Errico et al. | |
| 2003/0083747 A1 | 5/2003 | Winterbottom et al. | |
| 2003/0135275 A1 | 7/2003 | Garcia et al. | |
| 2003/0208273 A1 | 11/2003 | Eisermann et al. | |
| 2004/0030387 A1 | 2/2004 | Landry et al. | |
| 2004/0143332 A1 | 7/2004 | Krueger et al. | |
| 2004/0215198 A1 | 10/2004 | Marnay et al. | |
| 2004/0225295 A1 | 11/2004 | Zubok et al. | |
| 2005/0021042 A1 | 1/2005 | Marnay et al. | |
| 2005/0143747 A1 | 6/2005 | Zubok et al. | |
| 2005/0143749 A1 | 6/2005 | Zalenski et al. | |
| 2005/0165408 A1 | 7/2005 | Puno et al. | |
| 2005/0228500 A1 | 10/2005 | Kim et al. | |
| 2005/0251260 A1 | 11/2005 | Gerber et al. | |
| 2006/0030856 A1 | 2/2006 | Drewry et al. | |
| 2006/0030860 A1 | 2/2006 | Peterman | |
| 2006/0064100 A1 | 3/2006 | Bertagnoli et al. | |
| 2006/0089656 A1 | 4/2006 | Allard et al. | |
| 2006/0100633 A1 | 5/2006 | Michelson | |
| 2006/0149273 A1 | 7/2006 | Ross et al. | |
| 2006/0241641 A1 | 10/2006 | Albans et al. | |
| 2007/0016221 A1 | 1/2007 | Beyersdorff et al. | |
| 2007/0162134 A1 | 7/2007 | Marnay | |

FOREIGN PATENT DOCUMENTS

| | | |
|---|---|---|
| DE | 2263842 A1 | 7/1974 |
| DE | 2804936 A1 | 8/1979 |
| DE | 3023353 | 4/1981 |
| DE | 3526742 A1 | 1/1987 |
| DE | 4328690 B4 | 3/1995 |
| DE | 29916078 U1 | 11/1999 |
| EP | 0077159 A1 | 4/1983 |
| EP | 0471821 B1 | 2/1992 |
| EP | 0333990 B1 | 7/1993 |
| EP | 0712607 B1 | 2/2002 |
| FR | 2718635 A1 | 10/1995 |
| FR | 2724108 A1 | 3/1996 |
| FR | 2737656 | 2/1997 |
| FR | 2742653 A1 | 6/1997 |
| FR | 2795945 A1 | 1/2001 |
| JP | 2-261446 A | 10/1990 |
| WO | WO 91/13598 A1 | 9/1991 |
| WO | WO 98/34552 A1 | 8/1998 |
| WO | WO 01/01893 A1 | 1/2001 |
| WO | WO 01/19295 A1 | 3/2001 |
| WO | WO 02/071986 A2 | 9/2002 |
| WO | WO 03/053290 A1 | 7/2003 |

OTHER PUBLICATIONS

English abstract of cited reference, DE 3023353 A1, Apr. 1981, 1 page.

English abstract of cited reference, EP 0333990 B1, Jul. 1993, 1 page.

English abstract of cited reference, FR 2724108 A1, Mar. 1996, 1 page.

English abstract of cited reference, FR 2742653 A1, Jun. 1997, 1 page.

English abstract of cited reference, FR 2795945 A1, Jan. 2001, 1 page.

English abstract of cited reference, JP 2261446 A, Oct. 1990, 1 page.

In the United States Patent and Trademark Office, in Re. U.S. Appl. No. 10/070,823, Advisory Action dated Jun. 22, 2006.

In the United States Patent and Trademark Office, in Re. U.S. Appl. No. 10/070,823, Notice of Allowance dated Jul. 24, 2006.

In the United States Patent and Trademark Office, in Re. U.S. Appl. No. 10/318,078, Issue Notice dated Mar. 28, 2007.

In the United States Patent and Trademark Office, in Re. U.S. Appl. No. 10/318,078, Notice of Allowance dated Feb. 26, 2007.

In the United States Patent and Trademark Office, in Re. U.S. Appl. No. 10/318,078, Advisory Action dated Dec. 29, 2006.

In the United States Patent and Trademark Office, in Re. U.S. Appl. No. 10/318,078, Advisory Action dated Mar. 28, 2005.

In the United States Patent and Trademark Office, in Re. U.S. Appl. No. 10/070,823, Examiner Interview Summary Record and Notice of Allowance dated Jul. 13, 2006.

In the United States Patent and Trademark Office, in Re. U.S. Appl. No. 10/070,823, Non-final office action dated Sep. 23, 2004.

In the United States Patent and Trademark Office, in Re. U.S. Appl. No. 10/070,823, Final rejection dated Aug. 23, 2005.

In the United States Patent and Trademark Office, in Re. U.S. Appl. No. 10/318,078, Non-final office action dated Apr. 21, 2004.

In the United States Patent and Trademark Office, in Re. U.S. Appl. No. 10/318,078, Final rejection dated Nov. 12, 2004.

In the United States Patent and Trademark Office, in Re. U.S. Appl. No. 10/318,078, Non-final office action dated Aug. 8, 2005.

In the United States Patent and Trademark Office, in Re. U.S. Appl. No. 10/318,078, Final rejection dated Aug. 1, 2006.

In the United States Patent and Trademark Office, in Re. U.S. Appl. No. 11/512,327, Non final Rejection dated Oct. 6, 2008.

In the United States Patent and Trademark Office, In Re. U.S. Appl. No. 11/512,327, Final Rejection dated Jun. 23, 2009.

In the United States Patent and Trademark Office, In Re. U.S. Appl. No. 10/947,660, filed Sep. 23, 2004: Non-Final Office Action dated Dec. 11, 2006.

In the United States Patent and Trademark Office, In Re. U.S. Appl. No. 10/947,660, filed Sep. 23, 2004: Non-Final Office Action dated Dec. 26, 2007.

In the United States Patent and Trademark Office, In Re. U.S. Appl. No. 10/947,660, filed Sep. 23, 2004: Non-Final Office Action dated Jul. 2, 2007.

In the United States Patent and Trademark Office, in Re. U.S. Appl. No. 10/947,660, filed Sep. 23, 2004: Non-Final Office Action dated Jul. 24, 2008.

In the United States Patent and Trademark Office, In Re. U.S. Appl. No. 10/947,660, filed Sep. 23, 2004: Notice of Allowance dated Feb. 9, 2009.

In the United States Patent and Trademark Office, In Re. U.S. Appl. No. 10/947,660, filed Sep. 23, 2004: Notice of Allowance dated Mar. 9, 2009.

In the United States Patent and Trademark Office, In Re. U.S. Appl. No. 10/947,660, filed Sep. 23, 2004: Notice of Issue dated May 27, 2009.

In the United States Patent and Trademark Office, In Re. U.S. Appl. No. 11/512,327, filed Aug. 30, 2006: Notice of Allowance dated Oct. 8, 2009.

In the United States Patent and Trademark Office, In Re. U.S. Appl. No. 10/622,535, filed Jul. 21, 2003: Notice of Allowance dated May 13, 2010, 4 pages.
In the United States Patent and Trademark Office, In Re. U.S. Appl. No. 10/622,535, filed Jul. 21, 2003:Reqest for Continued Examination dated Apr. 14, 2010, 3 pages.
In the United States Patent and Trademark Office, In Re. U.S. Appl. No. 10/622,535, filed Jul. 21, 2003: Notice of Allowance dated Mar. 23, 2010, 4 pages.
In the United States Patent and Trademark Office, In Re. U.S. Appl. No. 10/622,535, filed Jul. 21, 2003: Request for Continued Examination dated Mar. 1, 2010, 3 pages.
In the United States Patent and Trademark Office, In Re. U.S. Appl. No. 10/622,535, filed Jul. 21, 2003: Notice of Allowance dated Nov. 17, 2009, 4 pages.
In the United States Patent and Trademark Office, In Re. U.S. Appl. No. 10/622,535, filed Jul. 21, 2003: Notice of Allowance dated Jun. 16, 2009, 4 pages.
In the United States Patent and Trademark Office, In Re. U.S. Appl. No. 10/622,535, filed Jul. 21, 2003: Final Rejection dated Feb. 6, 2009, 7 pages.
In the United States Patent and Trademark Office, In Re. U.S. Appl. No. 10/622,535, filed Jul. 21, 2003: Non-Final Office Action dated Sep. 8, 2008, 6 pages.
In the United States Patent and Trademark Office, In Re. U.S. Appl. No. 10/622,535, filed Jul. 21, 2003: Non-Final Office Action dated Jan. 31, 2008, 6 pages.
In the United States Patent and Trademark Office, In Re. U.S. Appl. No. 10/622,535, filed Jul. 21, 2003: Non-Final Office Action dated Sep. 12, 2007, 6 pages.
In the United States Patent and Trademark Office, In Re. U.S. Appl. No. 10/622,535, filed Jul. 21, 2003: Non-Final Office Action dated 26, 2007, 6 pages.
In the United States Patent and Trademark Office, In Re. U.S. Appl. No. 10/622,535, filed Jul. 21, 2003: Non-Final Office Action dated Nov. 8, 2006, 6 pages.
In the United States Patent and Trademark Office, In Re. U.S. Appl. No. 10/622,535, filed Jul. 21, 2003: Final Rejection dated May 23, 2006, 6 pages.
In the United States Patent and Trademark Office, In Re. U.S. Appl. No. 10/622,535, filed Jul. 21, 2003: Non-Final Office Action dated Aug. 30, 2005, 7 pages.
In the United States Patent and Trademark Office, In Re. U.S. Appl. No. 10/622,535, filed Jul. 21, 2003: Non-Final Office Action, Restriction Requirement dated May 31, 2005, 5 pages.
In the United States Patent and Trademark Office, In Re. U.S. Appl. No. 10/622,535, filed Jul. 21, 2003: Non-Final Office Action, Restriction Requirement dated Dec. 8, 2004, 5 pages.

* cited by examiner

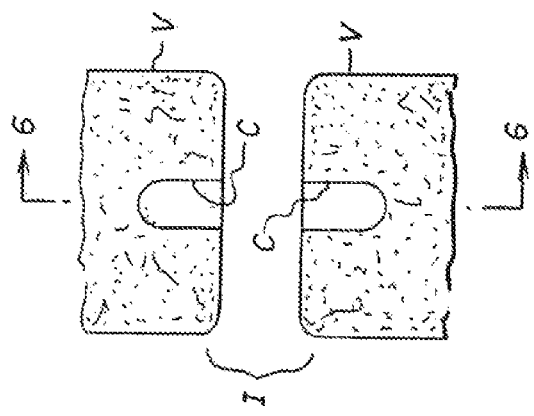
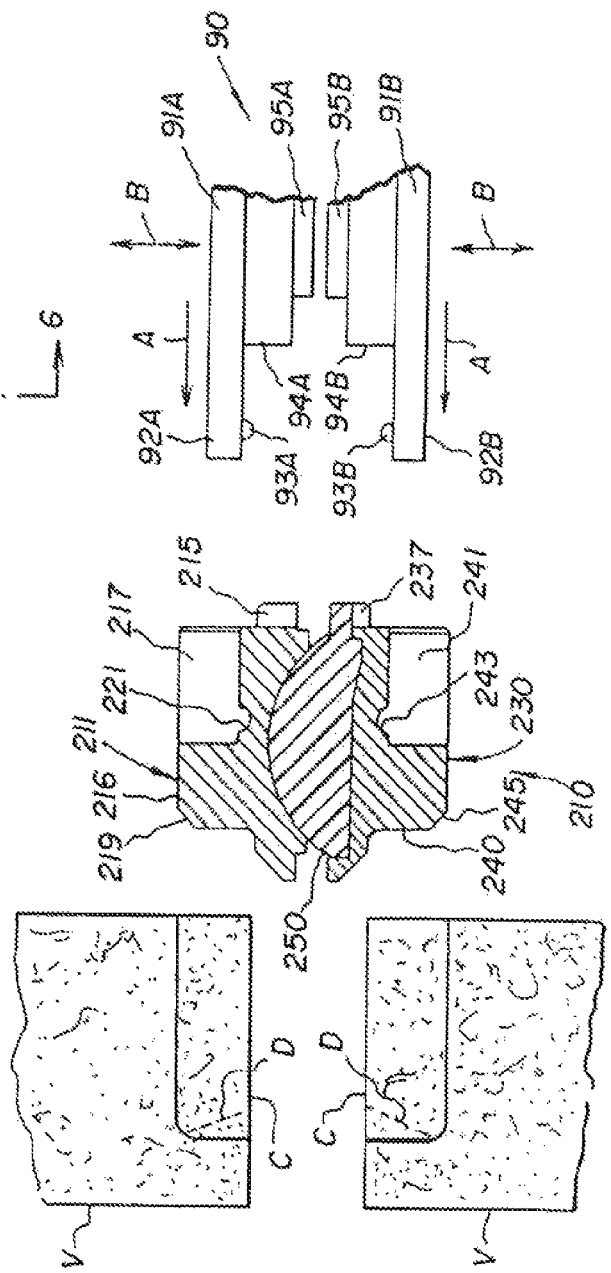
Fig. 5
Fig. 6

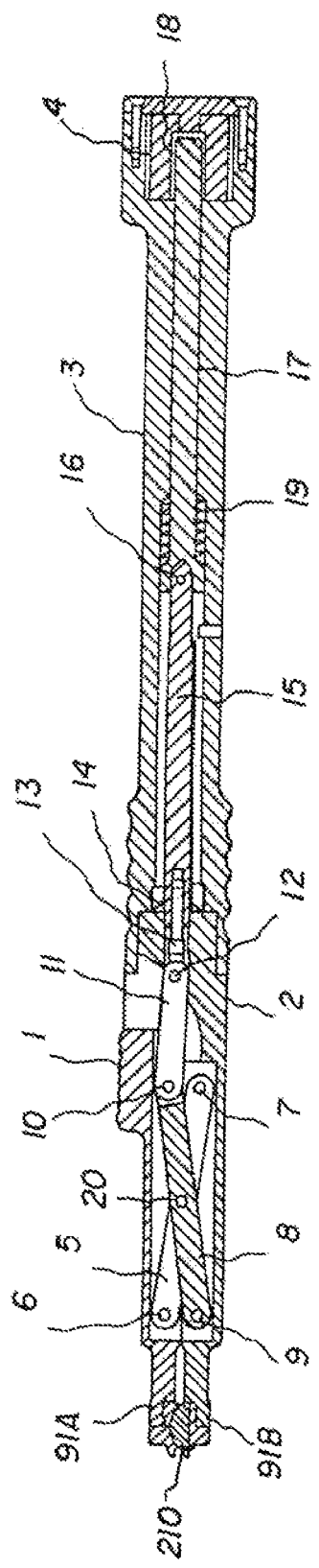
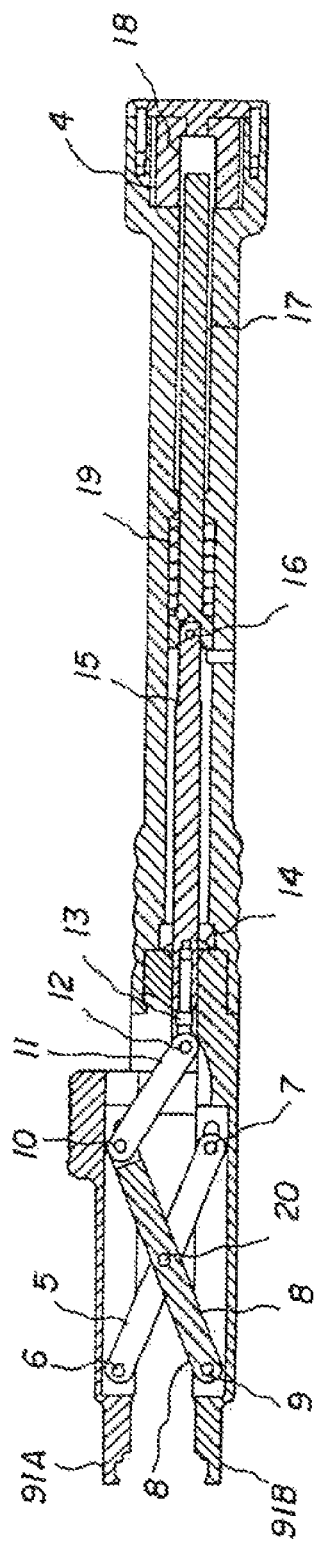
Fig. 11
Fig. 15

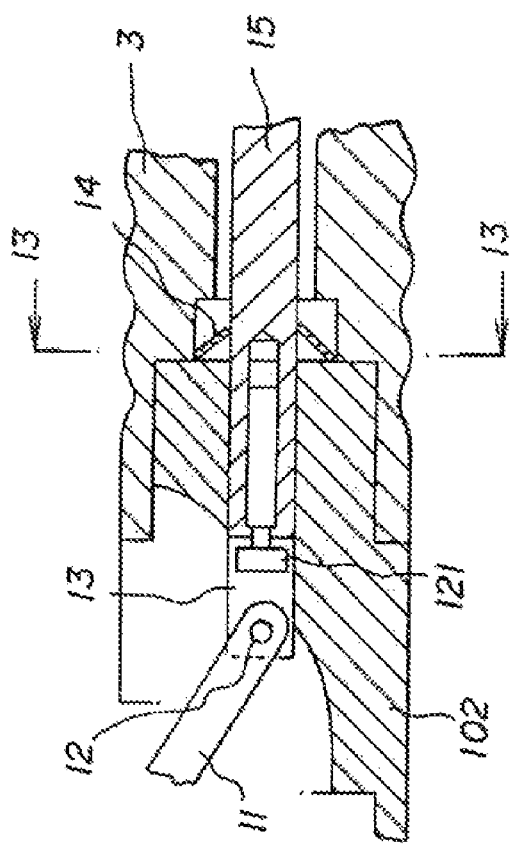
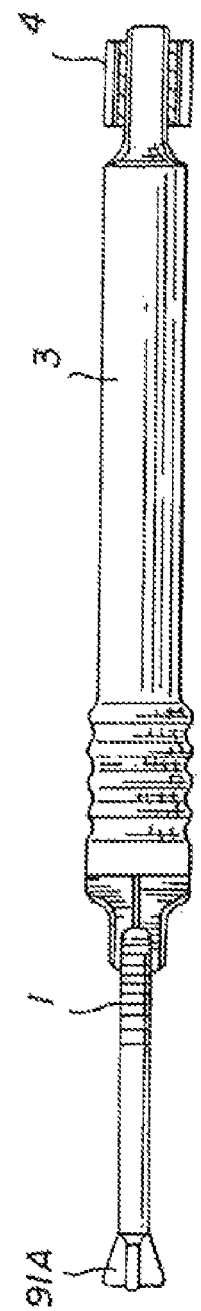

*Fig. 22*
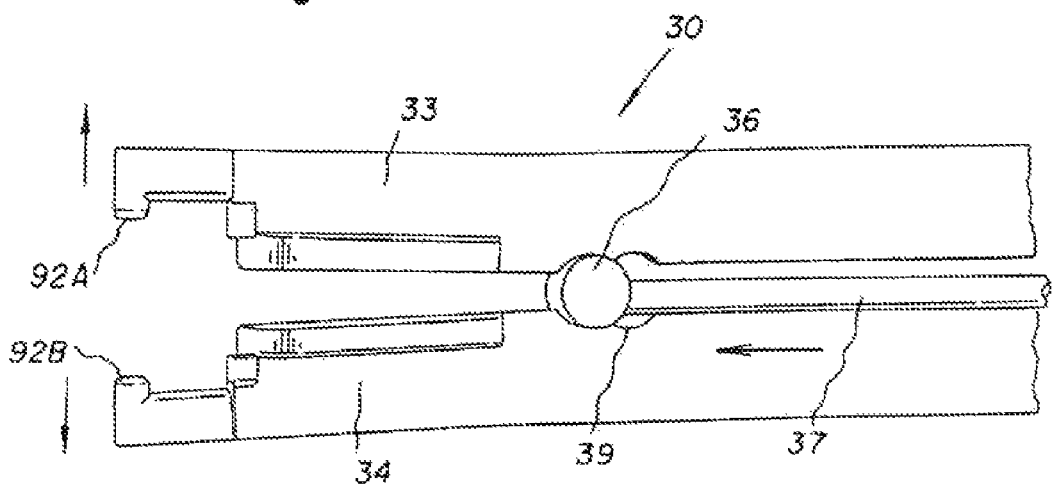
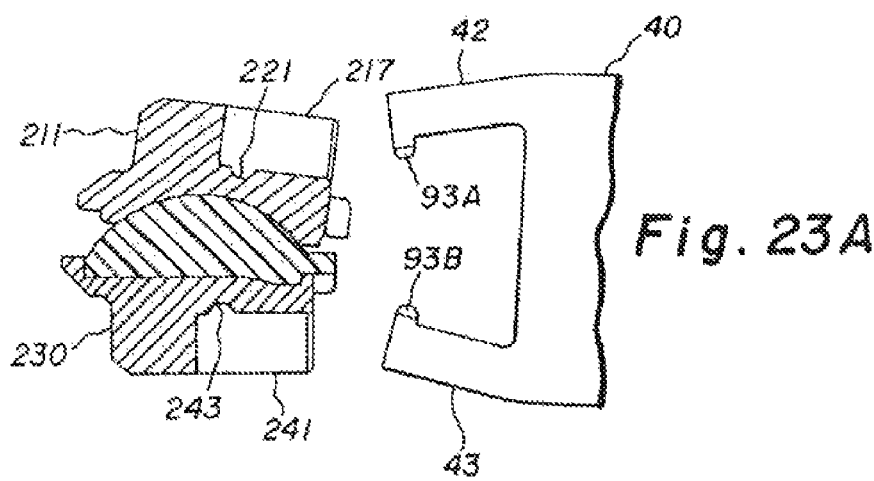
*Fig. 23A*
*Fig. 23*
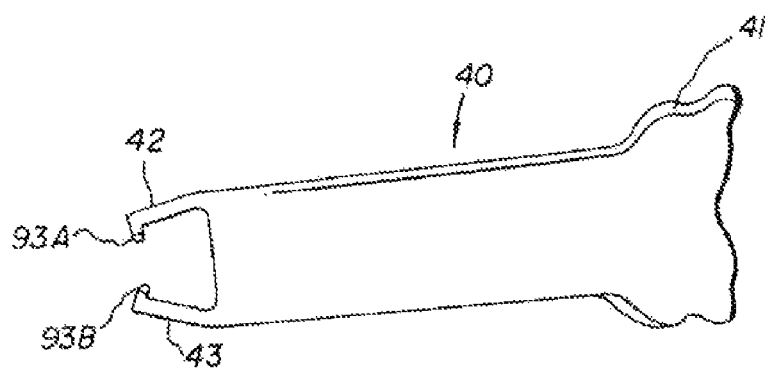

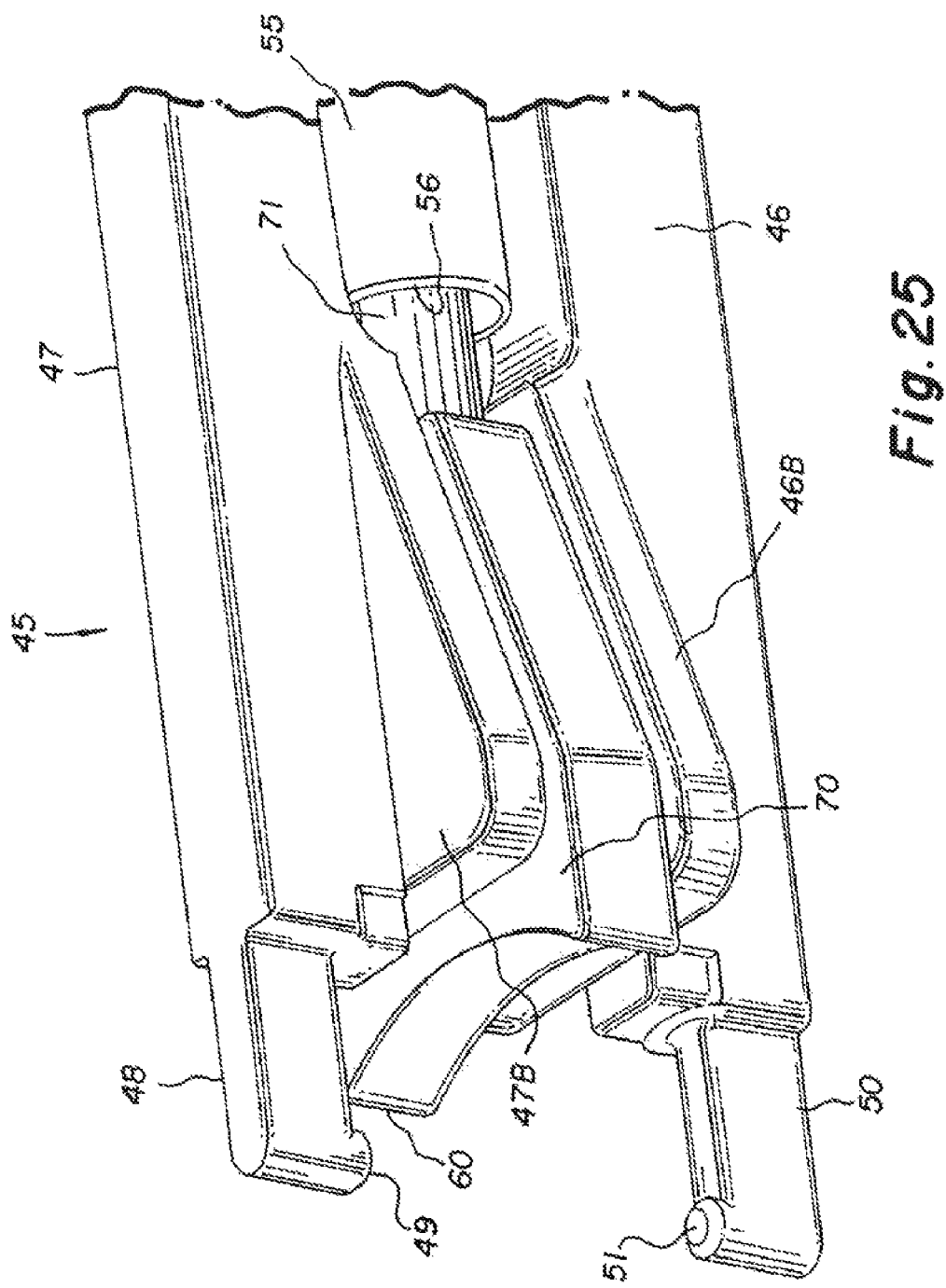

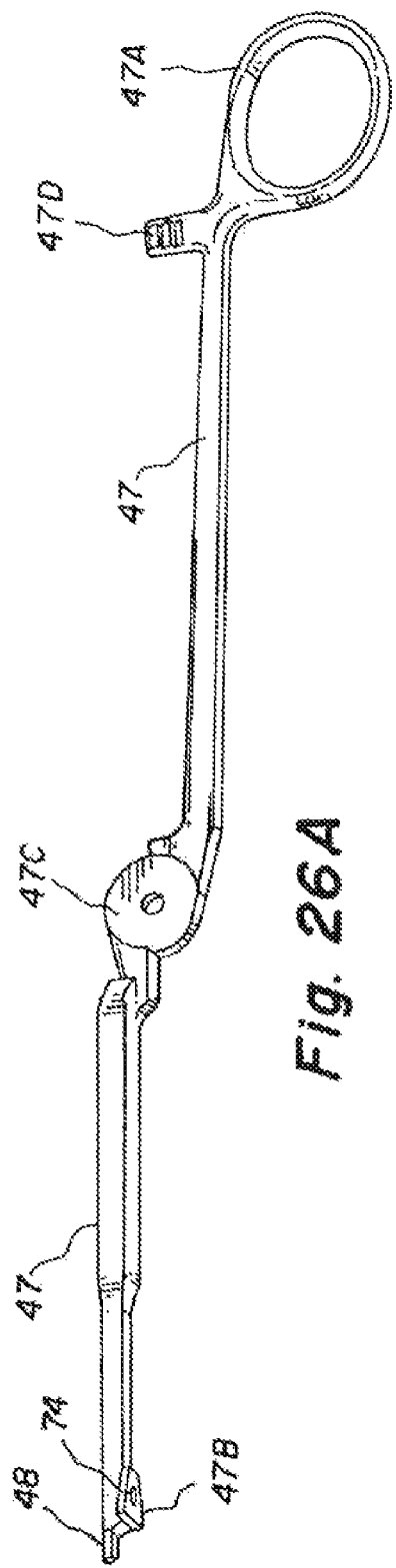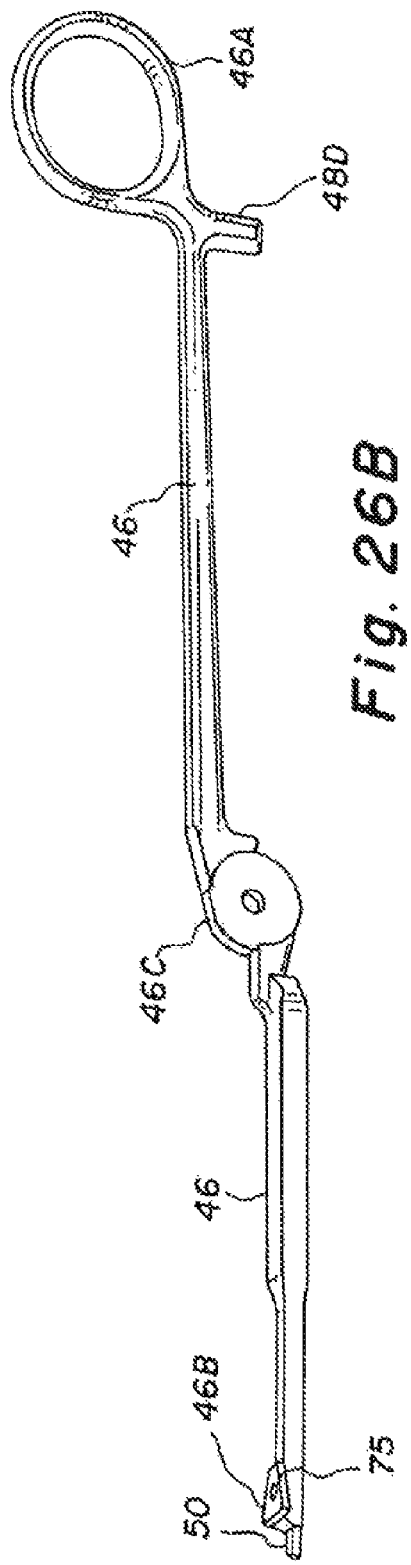
Fig. 26A
Fig. 26B

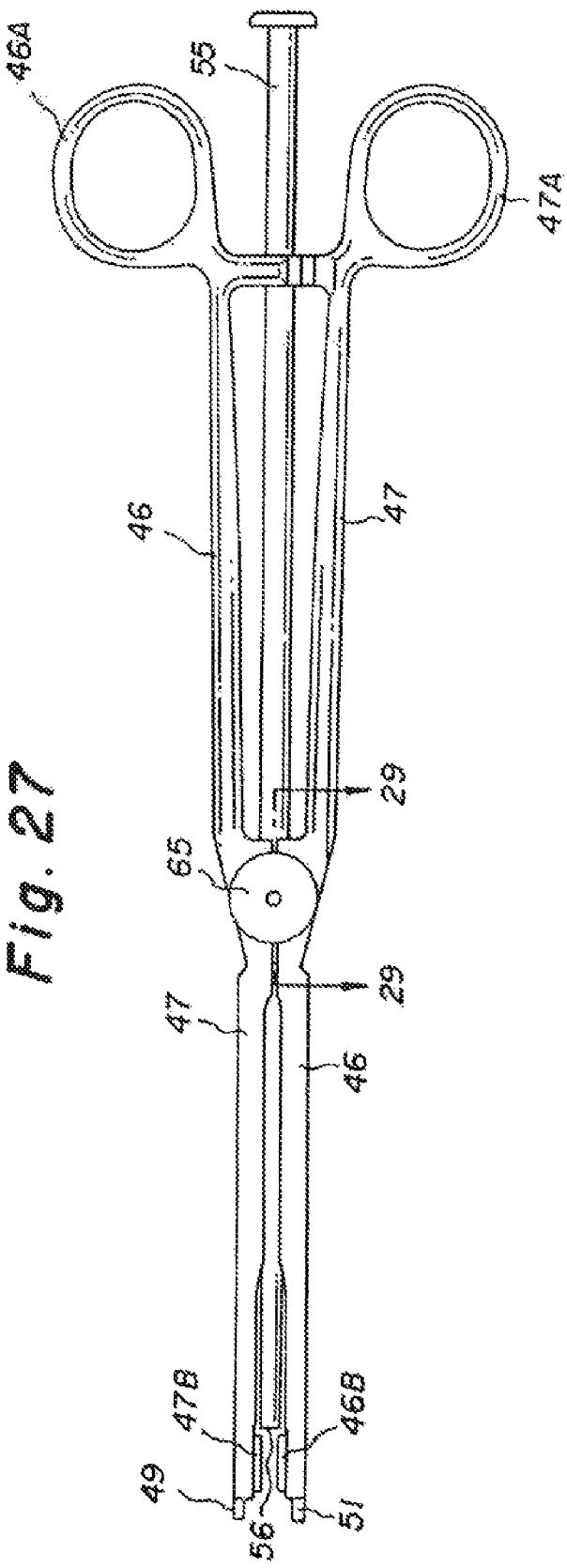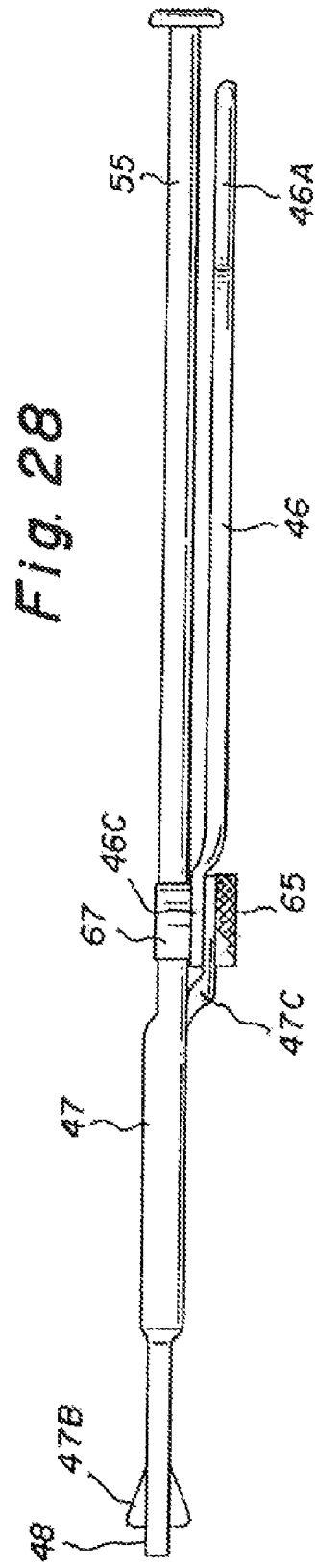

Fig. 34
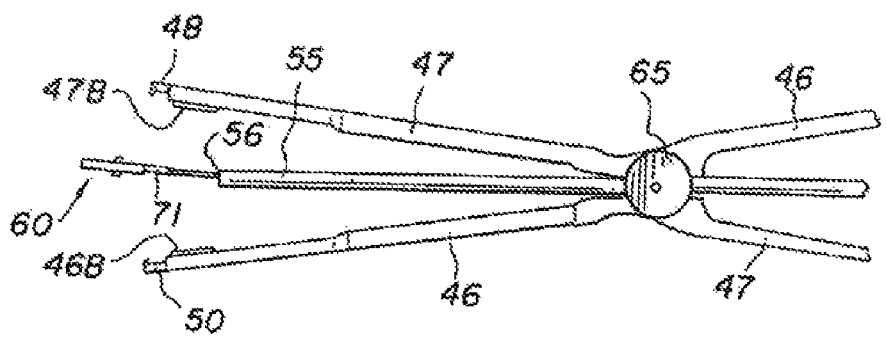
Fig. 35
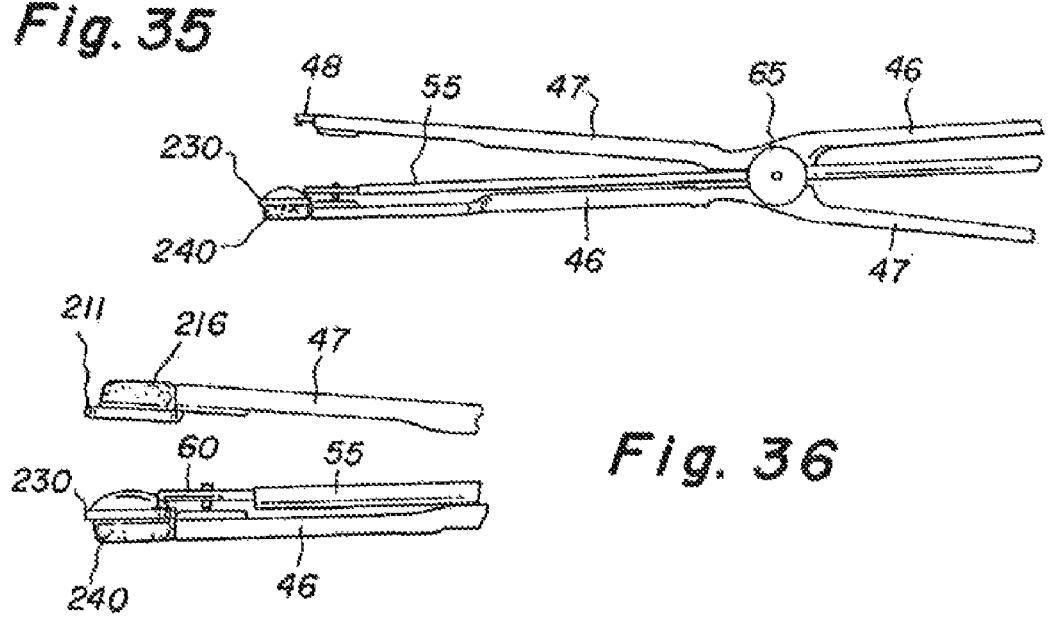
Fig. 36
Fig. 37
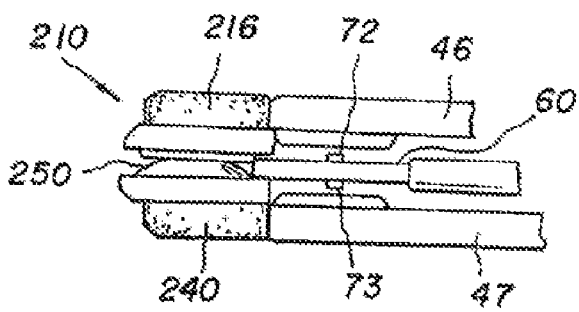

INSTRUMENTS AND METHOD FOR INSERTING AN INTERVERTEBRAL IMPLANT

CROSS REFERENCE TO RELATED APPLICATIONS

This patent application is a divisional application of, and claims priority to, U.S. patent application Ser. No. 10/622,535, filed Jul. 21, 2003, which is incorporated herein by reference in its entirety.

TECHNICAL FIELD

This invention relates to intervertebral implants, and more specifically, it relates to new and improved instruments and methods for inserting an intervertebral implant.

BACKGROUND

Currently, when it is necessary to completely remove a disc from between adjacent vertebrae, the conventional remedy is to fuse the adjacent vertebrae together. More recently, there have been important developments in the field of disc replacement, namely disc arthroplasty, which involve the insertion of an artificial intervertebral implant into the intervertebral space between adjacent vertebrae, and which allows limited universal movement of the adjacent vertebrae with respect to each other.

In conjunction with the development of such artificial intervertebral implants, instruments for inserting same were also developed. Such instruments are shown in Published Application No. WO 01/19295, published Mar. 22, 2001. An artificial intervertebral implant which was developed for use with said instruments is shown in Published Application No. WO 01/01893, published Jan. 11, 2001.

While the new instruments, methods and the artificial intervertebral implant shown in these publications represent a substantial improvement in the art, there exists a continuing need for improvements in the field of instruments and methods for inserting artificial intervertebral implants, especially in conjunction with newly developed artificial intervertebral implants.

One such area in need of further improvements includes instruments and methods for inserting artificial intervertebral implants into the cervical spine. This is because the cervical spine and the dimensions of the intervertebral spaces between the vertebrae are quite small. For example, the area of facing adjacent cervical vertebral surfaces may be only about 20% of the facing surfaces of the vertebrae in the lumbar region, thereby making this an extremely delicate area in which to insert an intervertebral implant.

SUMMARY

The purpose of the present invention is provide new and improved instruments and accompanying methods for inserting an intervertebral implant into the intervertebral space, especially in the cervical spine.

The intervertebral implant is normally inserted from the patient's anterior moving towards the patient's posterior. However, it is to be understood that the implant, the instruments and the method can also be designed and arranged to insert the implant laterally, i.e., from the side, in which case the implant will be constructed for such lateral movement and any cutouts in the adjacent vertebrae will be opened toward a lateral side. Although the terms "anterior" and "posterior" will sometimes be used in the conventional sense with respect to the patient's anatomy, for purposes of convenience, the invention will be described herein primarily with respect to more simple terminology which relates to the instruments and methods themselves. For example, in describing the invention, the terms "front" or "forward" mean the part of the instrument which faces toward the vertebrae or is moving in the direction of movement toward the vertebrae, while the words "back", "rear" or "rearward" refer to the end of the instrument farthest from the vertebrae or moving away from the vertebrae. Also, in this application, the words "upper" or "lower" or "uppermost" or "lowermost" or any other words describing the orientation of the intervertebral implant or the instruments or methods associated therewith are used only for convenience and are not intended to convey any limitation. More specifically, the parts of the implant, the instruments and/or the methods described in this application with reference to the upper part can in fact be positioned as the superior or inferior part within the patient's vertebrae, with the other of the two parts being the opposite part.

Although the instruments and method of the present invention have been developed and are particularly advantageous for the cervical spine, they are equally applicable for any location in the spine, including the lumbar spine. Thus, the instruments and method of the present invention will be described more generally without specifically identifying any particular portion of the spine.

The instruments and the methods of the present invention are particularly adapted for use with an intervertebral implant having upper and lower parts which undergo limited universal movement with respect to each other, with the upper and lower surfaces of the upper and lower parts engaging the adjacent vertebral surfaces, and wherein the implant has a keel extending from the vertebrae engaging surfaces of the upper and lower parts into cutouts formed in the adjacent vertebrae, and wherein these keels have recesses for receiving insertion instruments which are utilized for inserting the intervertebral implant into the intervertebral space with the keels located in the cutouts.

In accordance with a first aspect of the present invention, there is provided instruments and methods for inserting an intervertebral implant.

In accordance with a first embodiment and the accompanying method, an insertion instrument is provided which comprises a pair of arms connected to a body, and including a crossed linkage for separating the arms and then bringing them together so that the ends of the arms firmly engage the intervertebral implant, with the small outer extremities of the arms engaged within the recesses of the keels of the implant. A knob may be provided at the end remote from the implant engaging end, the knob being turnable to operate a crossed linkage to separate or close the arms of the instrument.

In accordance with another instrument and its accompanying method, there is provided a very simple, preferably plastic insertion instrument wherein the arms adjacent the implant engaging end are resiliently urged against the implant to secure it. In one embodiment, a thumb slide or other mechanism is provided for moving the arms apart from each other to the open position. In another embodiment, the plastic insertion instrument has a pair of arms of a resilient material which, in their relaxed state, are movable onto the implant after which, as they are moved farther onto the implant and into indentations 221 and 223, they are moved farther apart, creating a resilient force which secures the arms onto the implant. In either embodiment, to remove the arms from the implant the instrument is simply grasped and forcibly removed from the implant. Owing to its resilient nature, it comes out of the keel of the implant without harming the implant.

In accordance with another embodiment of an insertion instrument and its accompanying method, there is provided a scissors like insertion instrument, wherein two pivotally mounted scissors like arms have at the implant engaging ends thereof a structure, which like the above described insertion instrument embodiment, engages within the recesses of the keels of the implant. In addition, this embodiment includes a spacer which is movable to a position between the upper and lower parts of the implant to stabilize the implant as it is being held by the upper and lower arms and/or to create anatomical angulation. The spacer is removably secured to the scissors like insertion instrument so that spacers of different sizes may be provided for different size implants.

Thus, it is an object of the present invention to provide new and improved instruments for inserting an intervertebral implant.

It is another object of the present invention to provide new and improved methods for inserting an intervertebral implant.

These and other objects of the present invention will be apparent from the detailed description to follow, together with the accompanying drawings.

BRIEF DESCRIPTION OF THE DRAWINGS

Preferred embodiments of the invention will now be described by way of example with reference to the accompanying drawings, wherein:

FIG. 5 is a schematic view of a pair of adjacent vertebrae prepared to receive an implant using the instruments and in accordance with the method of the present invention;

FIG. 6 illustrates the vertebrae of FIG. 5, viewed in the direction of line 6-6 of FIG. 5 and showing the assembled implant positioned to be inserted and showing a portion of an insertion instrument;

FIG. 11 is a longitudinal cross sectional view of FIG. 10;

FIG. 12 is an enlarged view of a portion of FIG. 11;

FIG. 15 is a longitudinal cross sectional view similar to FIG. 11, but showing the insertion instrument in an opened position;

FIG. 16 is a top plan view of FIG. 10;

FIG. 22 is an enlarged view of the end of FIG. 21, showing the parts in a moved position;

FIG. 23 is a view similar to FIG. 20, but showing another embodiment of an insertion instrument;

FIG. 23A illustrates a method of attaching an implant to the insertion instrument of FIG. 23;

FIG. 25 is an enlarged perspective view of the implant engaging end of FIG. 24;

FIGS. 26A and 26B show respectively the two arms of the insertion instrument of FIG. 24;

FIG. 27 is a side elevational view of the insertion instrument of FIG. 24;

FIG. 28 is a top plan view of FIG. 27;

FIGS. 34-37 show different steps in the operation of the insertion instrument of FIGS. 24-33, wherein FIG. 37 is greatly enlarged relative to FIGS. 34 36.

DETAILED DESCRIPTION

Figure 1:
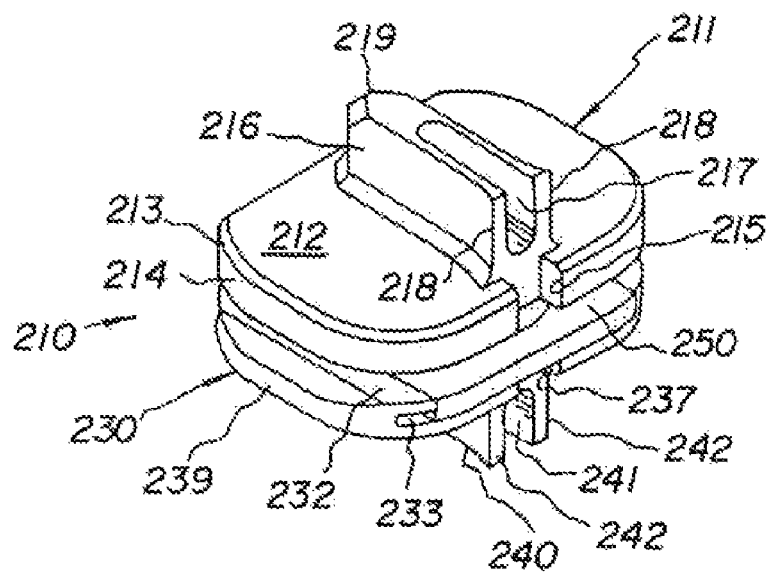
FIG. 1 is a perspective view of an intervertebral implant of the type which can be inserted by the instruments and method of the present invention.

Referring now to the drawings, like elements are represented by like numerals throughout the several views.

Figure 2:
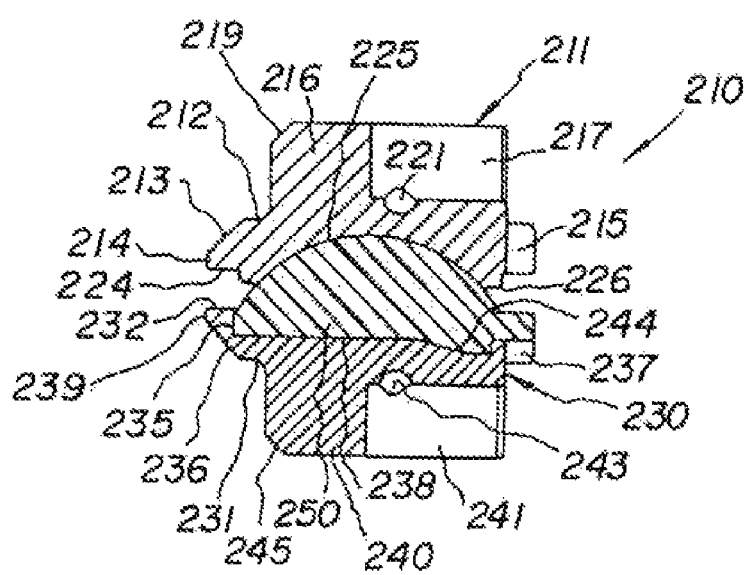
FIG. 2 is a central cross sectional view of FIG. 1.
Figure 3:
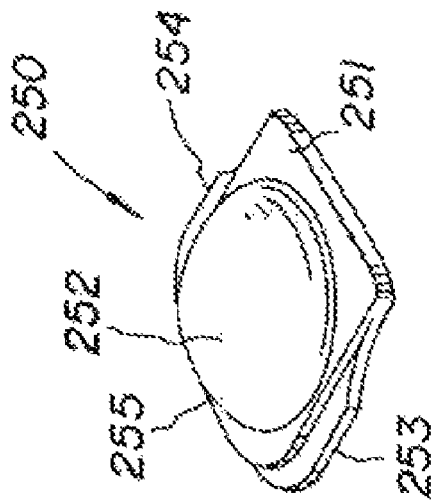
FIG. 3 is a top perspective view of the lower part of implant of FIG. 1.
Figure 4:
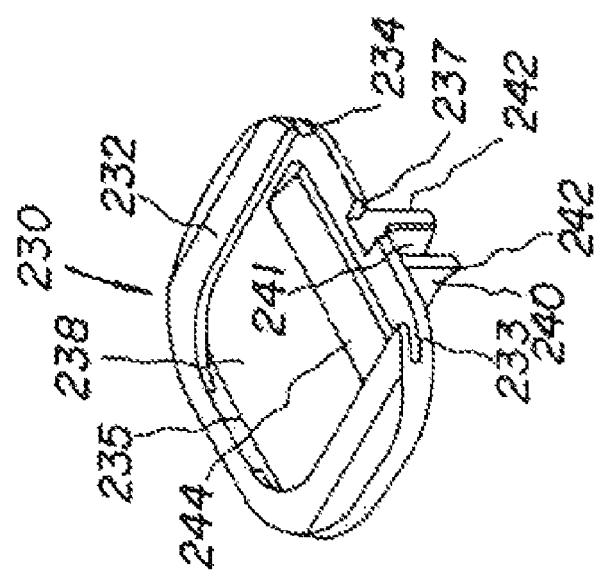
FIG. 4 is a top perspective view of the plastic inlay of the implant of FIG. 1.

FIGS. 1 4 illustrate the implant constructed to be inserted using the instruments and in accordance with the method of the present invention. FIGS. 1 and 2 illustrate an assembled intervertebral implant 210 including an upper part 211 and a lower part 230 and a plastic inlay 250 located therebetween but essentially connected to the lower part 230. FIG. 3 illustrates in detail the lower part 230 and FIG. 4 illustrates in detail the plastic inlay 250 which is adapted to be connected to the lower part 230 in a manner to be described below.

The upper part 211 includes an upper surface 212 which engages and supports the adjacent vertebral surface. Upper surface 212 is bounded by edges which are slightly beveled all the way around as shown at 213 with the largest portion of the bevel being shown along the front surface. Below the beveled edge 213, the upper part is bounded by a surrounding side wall 214 which has a front support cutout 215. Thus, in this figure, the keels as discussed below are shown oriented front to back, with the solid portion of the keels facing front and the insertion engaging recess facing rearwardly.

Rising above the upper surface 212 of the upper part 211 is a keel 216 which includes a recess 217 formed therein. This recess is opened upwardly and rearwardly. Referring to FIG. 2, this recess includes an indentation 221 in the base thereof. The front end of keel 216 comprises a V shaped upper bevel 219. Referring to FIG. 1, the lower portion of the front end of the keel is in the form of a V shaped bevel 220. The two V shaped bevels 219 and 220 provide a front end which is "arrow" shaped in order to facilitate insertion of the keel into a cutout formed in the adjacent vertebrae. The rear opening of the recess is flared at 218 to anchor the rear end of the keel 216 in its cutout in the adjacent vertebrae.

The upper part 211 includes a lower plane inner surface 224 which includes a raised rim 226 which defines a concave spherical portion 225. This spherical portion 225 mates with an upper convex surface 252 of the plastic inlay 250.

The lower part 230 includes a lower vertebrae supporting and engaging surface 231 and an inner upper surface 232. This lower part includes grooves 233 and 234 formed in the interior side wall thereof beneath surface 232 and above a base surface 238. A substantially flat wall 235 extends upwardly from the base surface 238 to the upper surface 232.

The lower part 230 includes a back support cutout 237. A keel 240 rises upwardly (or in the usual orientation, extends downwardly) from lower surface 231. This keel includes a recess 241 which opens downwardly and rearwardly and has a flared entrance at 242 which serves the same function as flared entrance 218, i.e., to facilitate engagement of the rear end of the keel within its cutout in the vertebrae. Recess 241 opens downwardly and rearwardly and includes an indentation 243. At its front end, the keel 240 includes a V shaped lower bevel 245 and a V shaped vertical portion (not shown) which together provide an "arrow" shaped front end to facilitate insertion of the keel into its cutout formed in the adjacent vertebrae. Referring to FIGS. 3 and 4, the plastic inlay 250 includes a pair of side flanges 253 and 254 which slide into the grooves 233 and 234 in the lower part. The bottom of the plastic inlay 250 may include a projection (visible in FIG. 2) which snaps into place in the recess 244 formed in the base surface 238 when the plastic inlay 250 is inserted into the lower part 230.

The intervertebral implant shown in FIGS. 1 4 and to be inserted by the instruments and method of the present invention has been designed primarily for insertion in the cervical spine. When viewed in plan view, this implant would be approximately 12 16 mm in width and approximately 15 19 mm in length. It has been found practical to provide three different sizes, 15 mm×19 mm, 14 mm×17 mm and 16 mm×19 mm. The height of the implant, meaning the height from the upper surface 212 of the upper part to the lower surface 231 of the lower part, would normally be between 5 mm and 9 mm. While this implant has been designed especially for application to the more delicate smaller cervical spine, the principles described herein are also applicable to intervertebral implants of a different size and design, such as for use in the lumbar spine.

The upper and lower parts are made of a suitable material such as titanium, cobalt chromium molybdenum, stainless steel or ceramics. The upper surface of the upper part and the lower surface of the lower part as well as the side surfaces of the keels are coated with a porous coating of titanium. The porosity of the coating ideally permits vascularization and osteoplast formation with subsequent bony on growth.

Before the instruments of the present invention can be used and the methods of the present invention commenced to insert an implant, it is of course necessary to prepare the patient by providing access to and cleaning out the relevant intervertebral space. Once such preparation has been completed, trial implants are inserted into the intervertebral space to determine which trial implant is the correct one, thereby determining the size of the implant which is to be inserted therein. Trial implants for the cervical spine may be provided in three different surface areas, i.e., when viewed in plan view, to match the three basic sizes of the implants, i.e., 12 mm×15 mm, 14 mm×17 mm and 16 mm×19 mm. Each of these three surface areas could then be provided in five different heights from 5 mm to 9 mm, inclusive, thus providing a set of 15 trial implants. Cutouts would then be formed in the adjacent vertebrae to receive the keels.

Insertion instruments and methods of the present invention are then used for inserting the implant into the intervertebral space.

Figure 9:
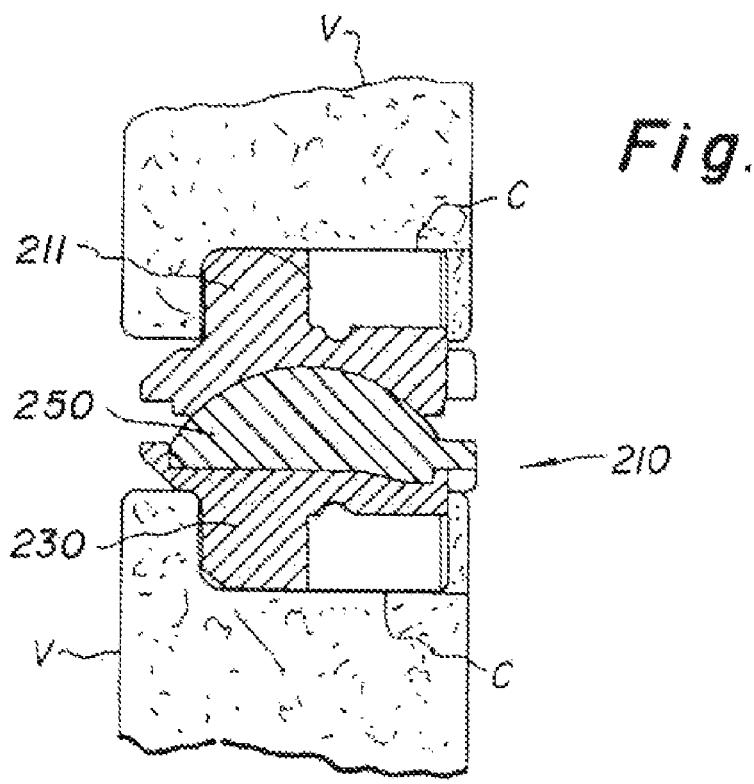
FIG. 9 illustrates the vertebrae with the implant in place and the insertion instrument removed.

The insertion process is shown and described generally in FIGS. 5 9. FIG. 5 is an anterior view of a pair of adjacent vertebrae V on opposite sides of a cleaned out intervertebral space I. In preparation for insertion of the intervertebral implant, cutouts C will have been formed. As shown in FIG. 6, these cutouts start from the anterior of the vertebrae and extend for most but not all of the distance towards the posterior of the vertebrae, each intersecting along its entire length with the surface of the vertebrae facing into the intervertebral space. If formed by a chisel, the posterior end may either be neutral or angled back as shown at line D. The depth of the cutouts C into the vertebrae V is established by the precisely controlled depth of a cutting tool.

FIG. 6 illustrates just to the right of the prepared adjacent vertebrae the intervertebral implant assembled and ready to be inserted, and to the right thereof is a schematic representation of a portion of an insertion instrument 90. The insertion instrument includes upper and lower arms 91A and 91B which are arranged to move towards and away from each other as indicated by arrows B in FIG. 6. One mechanism for moving the arms toward and away from each other is a crossed linkage 98 which is partially shown in FIG. 7. The upper and lower arms 91A and 91B include narrow keel engaging portions 92A and 92B which engage the recesses 217 and 241, respectively. These arms include towards their outer ends projections 93A and 93B which are constructed to be received in indentations 221 and 243, respectively. It will be noted that these keel engaging portions 92A and 92B are relatively narrow. In fact, it is contemplated that the entire width of each keel will be approximately 2 mm, thus allowing less than 2 mm for the actual recesses. The arms 91A and 91B also include lateral support surfaces 94A and 94B which, upon engagement of the instrument with the implant, will engage the front support cutouts 215 and 237. The arms 91A and 91B will be spaced apart just enough for the projections 93A and 93B to clear the bottoms of the recesses 217 and 241 until these projections reach the indentations 221 and 243, at which time the arms 91A and 91B will be moved towards each other such that the projections engage within the indentations and the lateral support surfaces 94A and 94B are engaged within the cutouts 215 and 237. At this position, abutment surfaces 95A and 95B on the upper and lower arms 91A and 91B, respectively, will abut each other, thus limiting further movement of the arms 91A and 91B towards each other.

To attach the implant to the insertion instrument, the implant is held in a suitable manner and the arms 92A and 92B are spread apart, moved into the recesses 217,241, and closed together such that the projections 93A and 93B engage indentations 221 and 243. Alternatively, the implant can be placed on the lower arm, with arm 92B within recess 241 and projection 93B in indentation 223, after which the upper arm 92A can be brought down into recess 217 with projection 93A entering indentation 221. With the implant thus attached to the insertion instrument, the insertion instrument moves the entire implant into the intervertebral space I with the keels 216 and 240 entering the cutouts C while the surfaces 212 and 231 posterior to and adjacent to the keels engage the adjacent vertebral surfaces.

Figure 8:
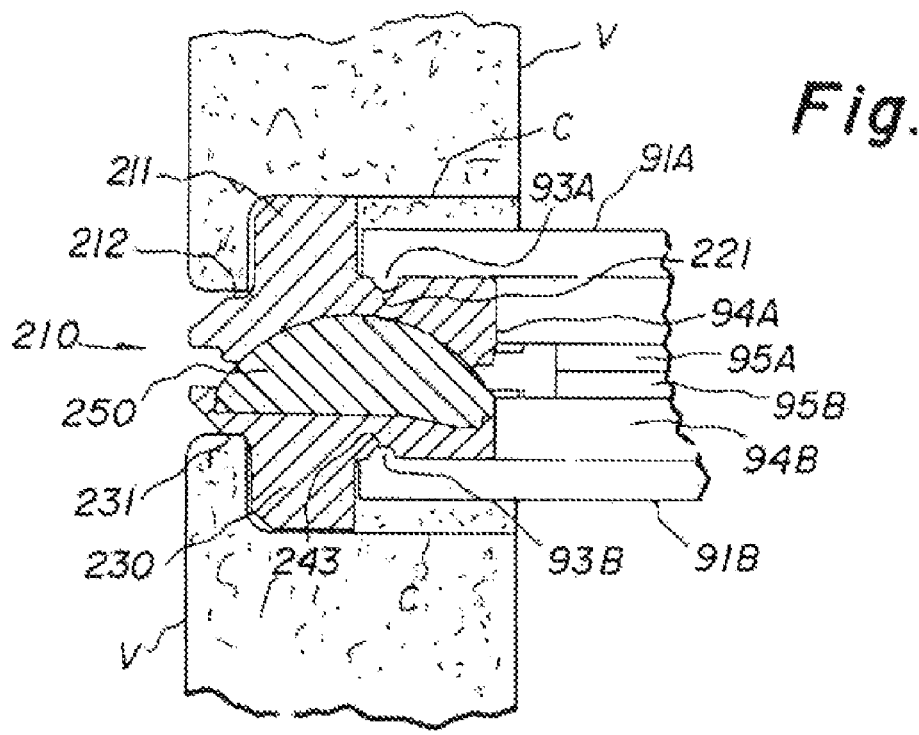
FIG. 8 illustrates the vertebrae of FIG. 5, with the implant in place therein and the portion of the insertion instrument still engaged with the implant.

It will be noted that in FIG. 8 there is a space above and below the arms 91A and 91B within the keel recesses 217 and 241, the vertical dimension of which spaces is greater than the height of the projections 93A and 93B, which would normally be about 1.2 mm. This is necessary so that the arms 91A and 91B can be moved upwardly and downwardly, respectively, away from the base of their respective recesses to free the projections from their respective indentations before the upper and lower arms 91A and 91B can move horizontally out of the cutouts, without engaging the vertebrae at the vertical extremities of the cutouts C. The arms 91A and 91B can then be moved out anteriorly from the implant, leaving the implant in place as shown in FIG. 9.

Figure 10:
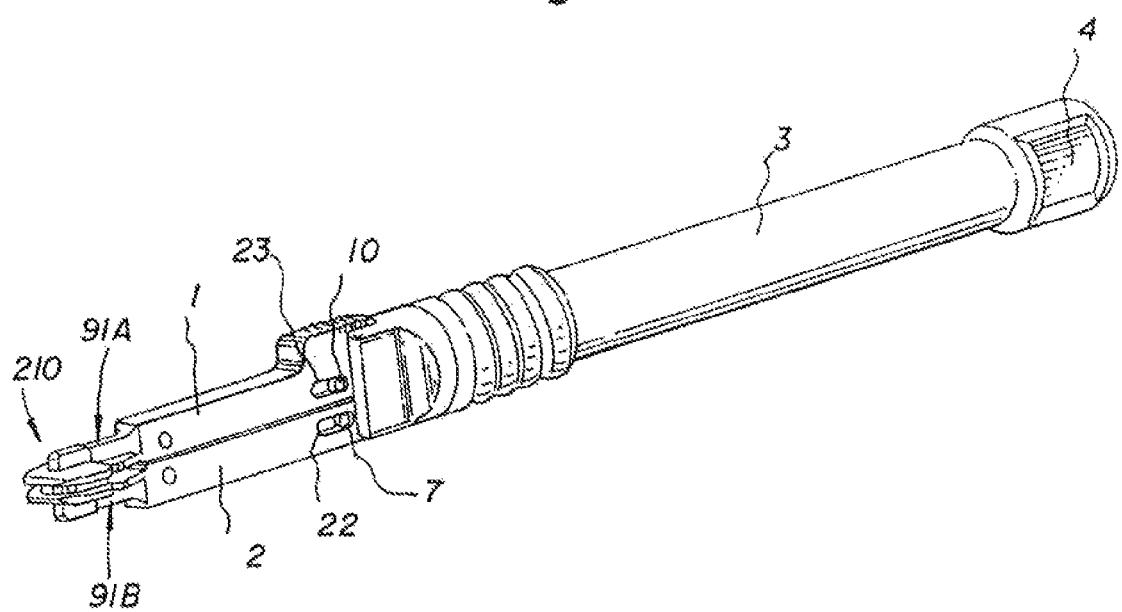
FIG. 10 is a perspective view of a first embodiment of an insertion instrument, shown in the closed position.

FIGS. 10 16 show a first embodiment of an insertion instrument.

Figure 7:
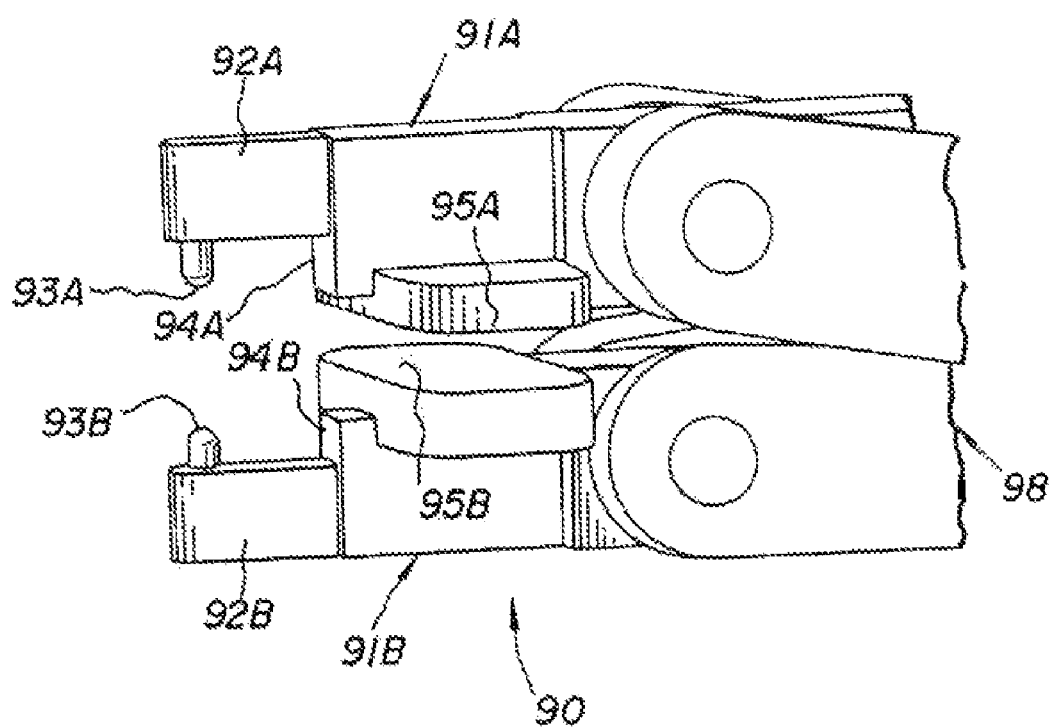
FIG. 7 illustrates in greater detail the portion of the insertion instrument shown in FIG. 6.

This crossed linkage instrument insertion instrument includes a body 3 having a control knob 4 at the rear end thereof and arms 1 and 2 at the forward end thereof. There is shown forward of these arms 1 and 2, the arms 91A and 91B of the insertion instrument which is shown in FIGS. 6, 7 and 8, with an assembled implant 210 being held thereby.

Figure 14:
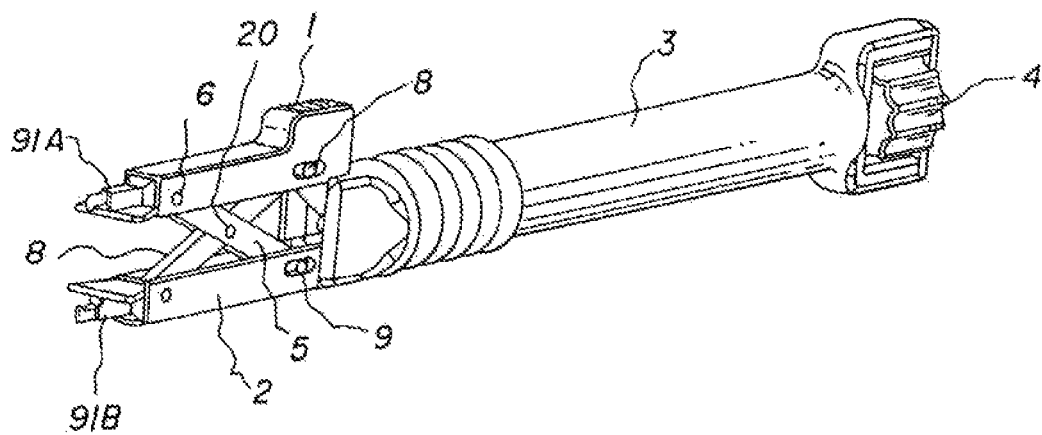
FIG. 14 is a perspective view of the insertion instrument of FIGS. 10 and 11, but shown in an opened position.

FIG. 11, like FIG. 10, shows the insertion instrument with the arms 1 and 2 in the closed position holding the implant 210. Referring to FIG. 11 which shows the insertion instrument in the closed position, as well as FIGS. 14 and 15 which show the insertion instrument in the opened position, it is seen that the arms 1 and 2 are operated to move towards and away from each other, or more specifically, to raise the arm 1 while the arm 2 is fixed with respect to the body 3. The mechanism for raising the arm 1 includes crossed linkage comprising a first link 5 having a pivot pin 6 at one end thereof and a pivot pin 7 at the other end thereof. A second link 8 has a pivot pin 9 at one end thereof and a second pin 10 at the opposite end thereof. As is seen in FIG. 10, the two rear pivot pins 7 and 10 can undergo limited horizontal movement within slots 22 and 23. A third link 11 is connected at one end to second link 8 by means of a pivot pin 10 and at its other end to a sleeve 13 by means of a pivot pin 12. Sleeve 13 is in turn attached to a threaded rod 15 which is attached at pin 16 to a square cross section rod 17 which is slidably received in square opening 18 in the knob 4. A spring 19 rests against a shoulder in the body 3 and urges the rods 15 and 16 to the left, i.e., to the opened position of the arms.

Figure 13:
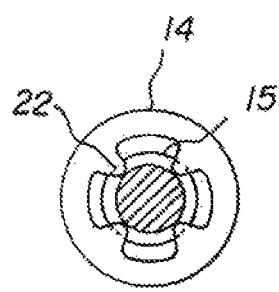
FIG. 13 is a partial cross sectional view taken along line 13-13 of FIG. 12.

The insertion instrument of FIGS. 10 16 operates as follows. Referring to FIGS. 12 and 13, the threaded rod 15 engages a bevel washer 14 which is held in a space between the right hand end of lower arm 2 (which at its far right hand end extends upwardly to cover virtually the entire circumference of the tool) and the left hand end of body portion 3. To open the instrument, i.e., to move from the position of FIGS. 10 and 11 to the position of FIGS. 14 and 15, the knob 4 is turned. The square recess 18 engages the square shaft 17, turning it and thus via pin 16, turning the threaded rod 15. This causes the rod 15 to move to the left via its threaded engagement with the bevel washer 14. This causes the end 21 of rod 15, which is rotatably received in sleeve 13 to move the sleeve 13 to the left, thereby also moving link 11 to the left. As is apparent by observing the positions of the various links in FIGS. 11 and 15, this leftward movement of link 11 moves all of the other links so as to move the upper arm 1 upwardly relative to the lower arm 2. To close this insertion instrument from the position of FIG. 15 to the position of FIGS. 10 and 11, thumb engaging portion of upper arm 1 is simply pressed down. This will move the link 11 downwardly and thus the sleeve 13 to the right. This in turn will move the threaded rod 15 to the right, allowing its threads to simply slip past the lobes 22 of the washer 14 (see FIG. 13).

Figure 17:
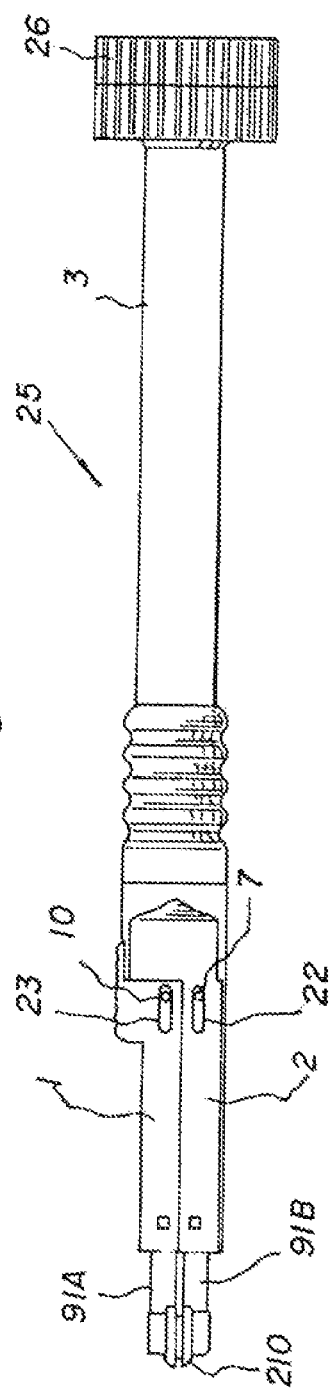
FIG. 17 is a longitudinal sectional view of another embodiment of an insertion instrument, shown in the closed position.
Figure 18:
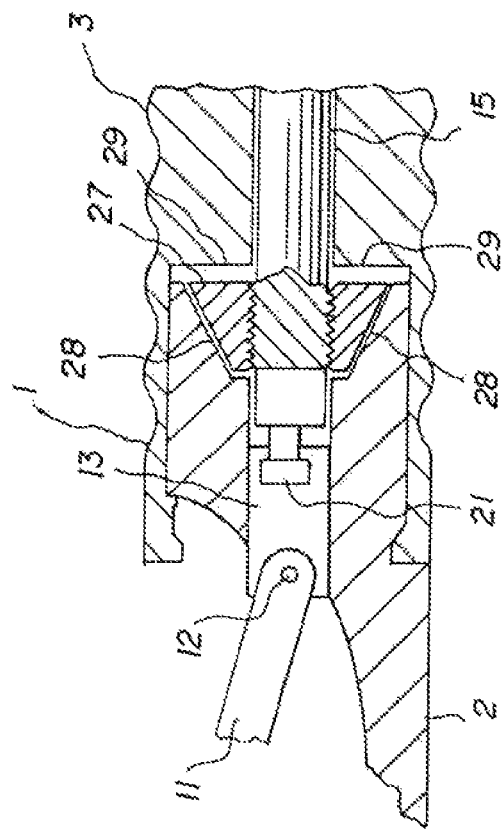
FIG. 18 is an enlarged view of a portion of FIG. 17, shown in cross section.

FIGS. 17 and 18 illustrate another embodiment 25 of a crossed linkage insertion instrument. This insertion instrument is similar to the insertion instrument of FIGS. 10 16 with the exception of a circular knob 26 at the right hand end thereof and the thread engaging mechanism which is shown in greater detail in FIG. 18. Thus, in FIGS. 17 and 18, elements which are identical to those shown in FIGS. 10 16 are represented by the same numerals.

Referring to FIG. 18, in this case the bevel washer 14 is replaced by a tapered washer or nut 27. To the left of nut 27, the taper frictionally engages a conical wall 28 formed on the right hand end of lower arm 2. Thus, when the threaded rod 15 is caused to move to the left by the turning of knob 26, the conical portion of nut 27 frictionally engages the conical surface 28 which prevents the nut 27 from rotating, whereby the threaded rod 15 is threaded through the nut 27 to move the sleeve 13 and hence the link 11 to the left to move the upper arm 1 upwardly in the same manner as described above with respect to the embodiment of FIGS. 35 39. To close the linkage, i.e., to move the arm 1 downwardly, once again the finger engaging top of arm 1 is grasped and pushed downwardly. As in the case of the previous embodiment, this will move the links in such a way as to move link 11 to the right. This moves the sleeve 13 and hence also the threaded rod 15 to the right. The washer 27 becomes disengaged from conical wall 28. The facing wall 29 of the body 3 cooperates in a low friction manner with the right hand side of nut 27 so it can spin, permitting simplified movement of the threaded rod 15 to the right, causing closing motion of the arm 1 on the arm 2 to the position as shown in FIG. 17. Attaching the implant to the instruments of FIGS. 10 18 and inserting the implant into the intervertebral space is essentially as described above with respect to FIGS. 5 9.

Figure 19:
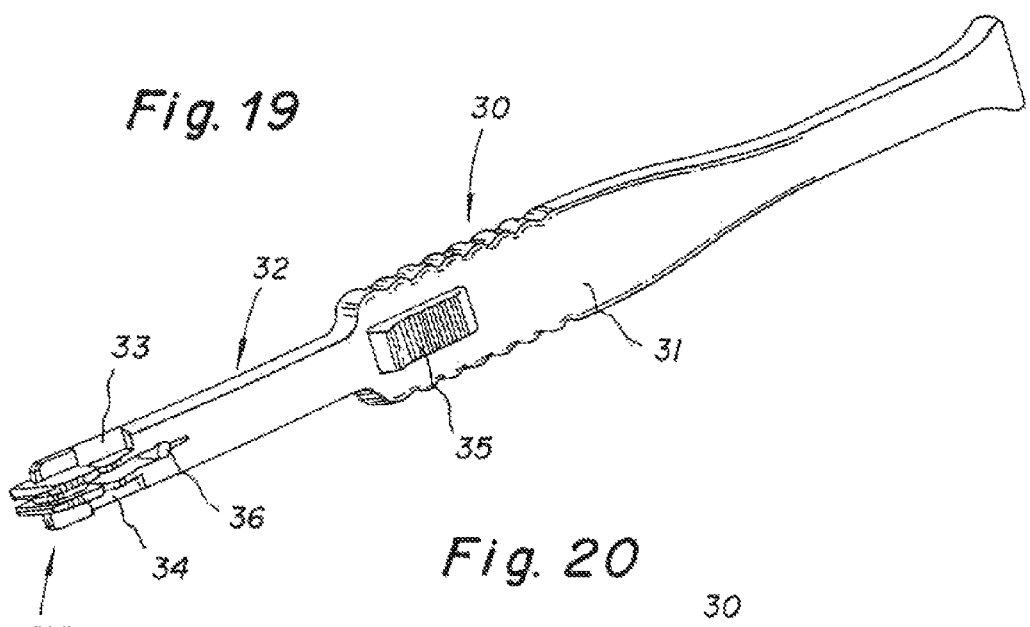
FIG. 19 is a perspective view of another embodiment of an insertion instrument, shown in the closed position.

FIGS. 19 22 show another embodiment 30 of an insertion instrument. This embodiment is extremely simple and hence economical. Basically, this insertion instrument 30 comprises a plastic body 31 having a front part 32 formed integrally with body 31 and comprising upper and lower arms 33 and 34. In FIG. 19, insertion instrument 30 is shown in its closed position holding an implant 210.

Figure 20:
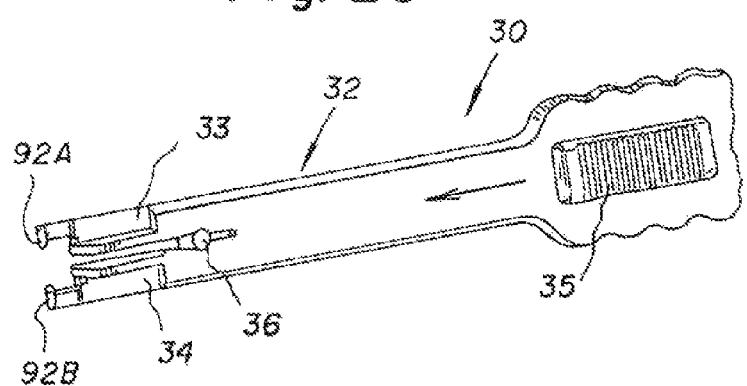
FIG. 20 is an enlarged view of the implant engaging end of FIG. 19.
Figure 21:
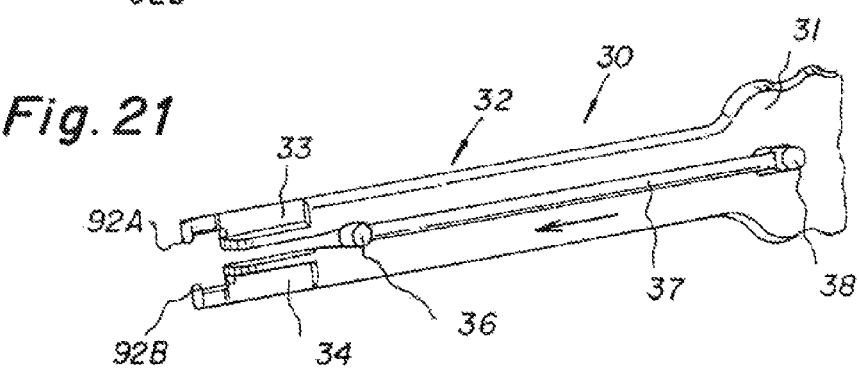
FIG. 21 is a view similar to FIG. 20, but with portions removed to illustrate interior features.

FIGS. 20 and 21 illustrate the front portion 32 of the insertion instrument 30. FIG. 20 shows a thumb slide 35 and a pin 36 while in FIG. 21 part of the side wall and the thumb slide 35 are removed, thus revealing the pin 38 which would be attached to the thumb slide 35 and the rod 37 which engages a pin 36. The two arms 33 and 34 are normally urged resiliently towards each other to a closed implant holding position. However, referring to FIG. 22, by moving the rod 37 to the left, the pin 36 rides out of its recess 39 and urges the arms 33 and 34 apart, thus opening the insertion instrument.

Attaching the implant to the instrument of FIGS. 19 22 and inserting the implant into the intervertebral space is essentially the same as described above with respect to FIGS. 5 9.

FIG. 23 illustrates another embodiment of an insertion instrument. This embodiment 40 is similar to the embodiment 30 of FIGS. 19 22 except that it is even more highly simplified. Forward of a body 41 is a front part 40 which comprises at the outer end thereof upper and lower arms 42 and 43 which are of a resilient material and in their rest state are spread apart as shown in FIG. 23. This embodiment includes no separate mechanism for separating the arms 42 and 43 from each other. To attach the implant to the instrument of FIG. 23, one would move the upper part of the implant about the spherical surface of plastic inlay 250 as shown in FIG. 23A, so that the front bottoms of the keels are slightly closer to each other than the distance between projections 42 and 43 in their relaxed state, as shown, arms 42 and 43 are then moved into the recesses until the projections 93A and 93B move into the indentations 221 and 243 and the top part rotates back to its correct position. As the top part rotates back to its correct position, the arms 42 and 43 are moved farther apart, thus creating the resilient force in the arms to secure them onto the implant. The insertion instrument 40 is made with a degree of resilience such that the insertion instrument 40 can simply be pulled out of the inserted implant, whereupon the projections 93A and 93B will simply ride up out of their respective indentations 221 and 243 without harm to the inserted implant. This is because after the implant has been inserted and the adjacent vertebrae relaxed (distention removed) so as to permit the adjacent vertebrae to move against the implant, the implant will then be held with a very strong force by the adjacent vertebrae such that the force of removing the instrument 40 will be relatively small by comparison such that the projections 93A and 93B can easily ride up out of their respective indentations, as described above.

Figure 24:
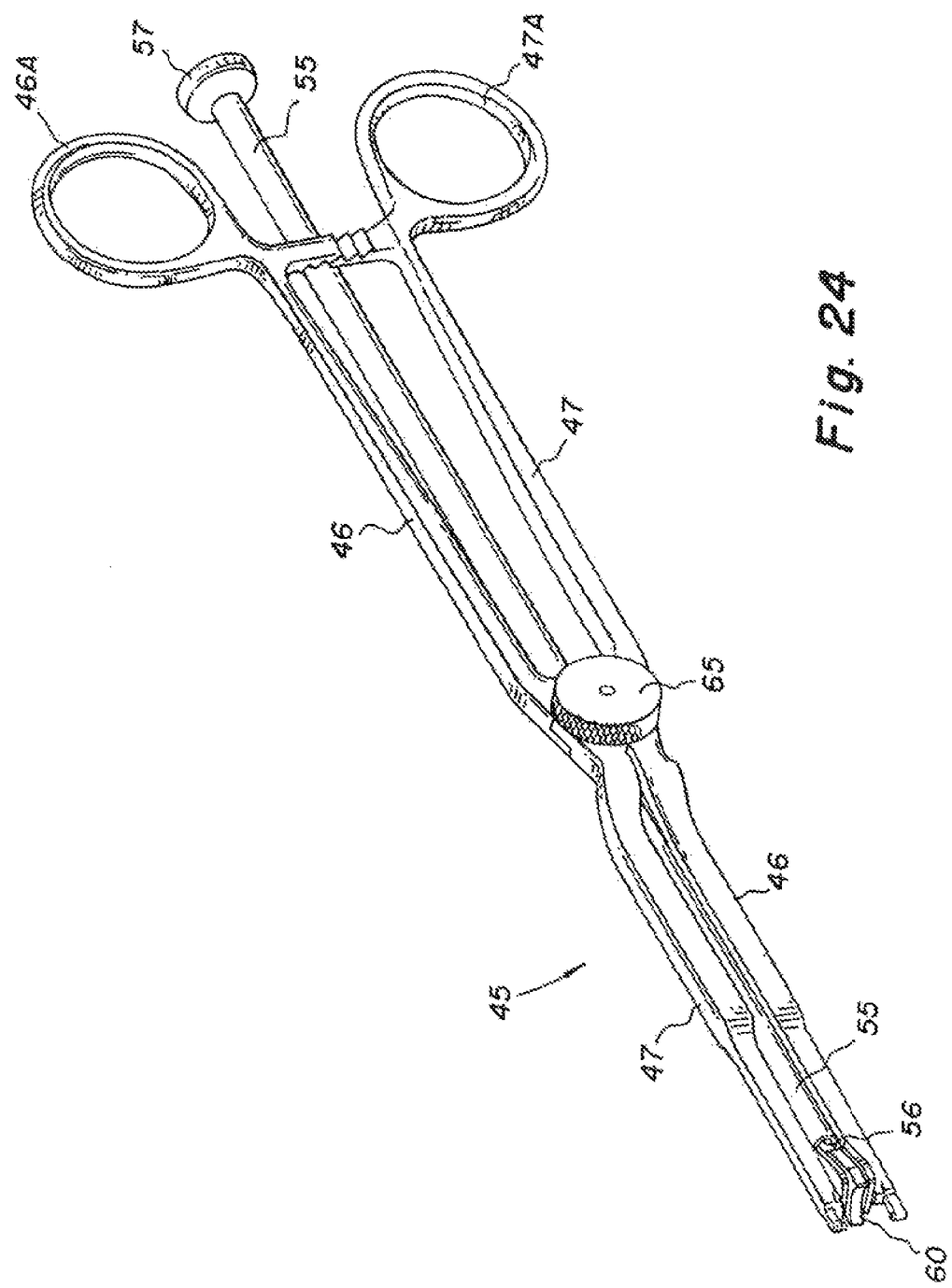
FIG. 24 is a perspective view of another embodiment of an insertion instrument.

Referring to FIGS. 24 and 25, there is shown in perspective view an entire insertion instrument 45 and an enlarged view of the forward end thereof, respectively. This insertion instrument includes a first arm 46 and a second arm 47, which arms are mounted on a common pivot in the manner of a scissors, which pivot is in the area of securing nut 65, as described in greater detail below. A spacer tube 55 runs the length of the instrument from a knob 57 at its rear end to an open end 56 at its opposite, forward end.

The two arms 46 and 47 are essentially coplanar rearward of the pivot connection and to one side of the spacer tube. These two arms then bend laterally in the vicinity of the pivot connection such that they become coplanar with the spacer tube 55 forward of their pivot connections.

At the forward end of this insertion instrument, as best seen in FIG. 25, each of the arms 46 and 47 have a narrow keel engaging end 50 and 48, respectively, each of which has at its end a projection 51 and 49, respectively, which engages the recesses 243 and 221 in the implants, respectively. Arm 47 has a generally flat spacer engaging member 47B and arm 46 has a similar generally flat spacer engaging member 46B.

Figure 30:
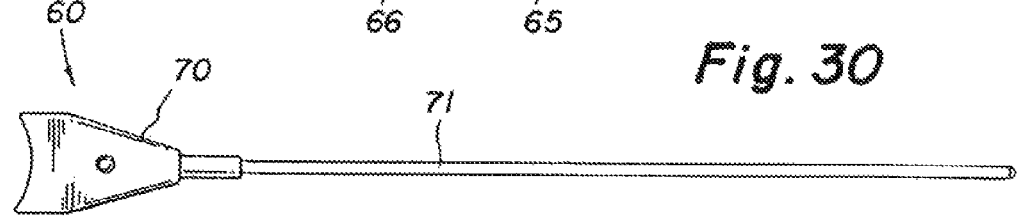
FIG. 30 is a top plan view of the spacer of FIG. 24.
Figure 31:
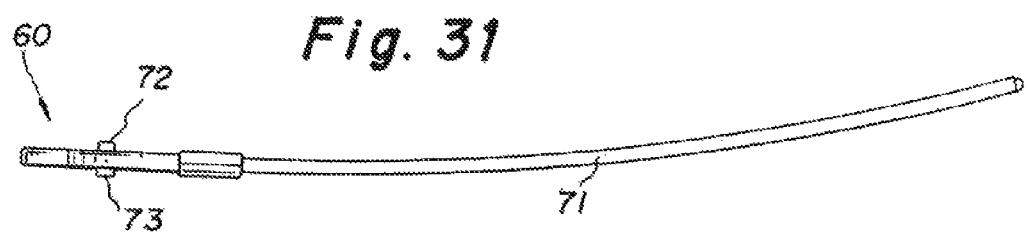
FIG. 31 is a side elevational view of the spacer of FIG. 30.

Referring to FIG. 25 as well as FIGS. 30 and 31, this insertion instrument includes a spacer 60 with an enlarged spacer head 70 and a shaft 71 which is removably secured in the spacer tube 55. The purpose of making the spacer removable is so that different size spacers can be utilized for different size implants.

FIGS. 26A and 26B show the two arms 47 and 46, respectively, separated from each other. The arm 47 includes a thumb/finger grip portion 47A, a central flat circular portion 46C and the previously described flat spacer engaging member 47B. This end, including narrow forward end 48 and member 47B engage the implant and the spacer from above. FIG. 26B shows the other arm 46 which includes portions similar to those of arm 47 including a thumb/finger grip portion 46A, a flat circular central portion 46C and a forward end including a narrow forward end 50 and a lower flat spacer engaging member 46B, wherein the members 46B and 50 engage the implant and spacer from below. The ridged locking flange 48D includes ridges on the opposite side thereof which, when lowered onto ridges 47D will lock the two arms together.

Figure 29:
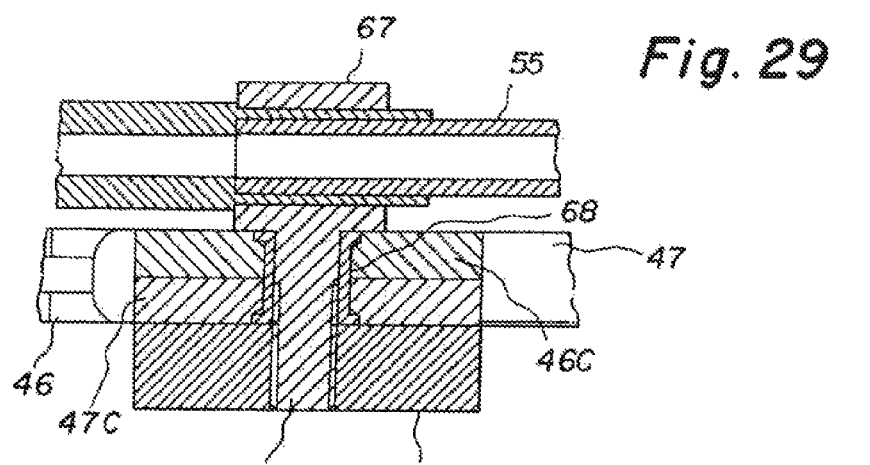
FIG. 29 is a partial cross sectional view taken along line 29-29 of FIG. 27.

Referring to FIGS. 27 29, it will be seen that the insertion instrument 45 is made by placing the two circular flat portions 46C and 47C against each other with the portion 47C closest to the securing nut 65 and the portion 46C closest to the tube 55, as best shown in FIG. 29. The two flat central portions 46C and 47C are secured together by a securing nut 65 and a shaft 66 which passes therethrough, through the openings in the flat central portions 46C and 47C and includes at the other end thereof a sleeve 67 which fixedly secures the forward and rear sections of the fixed spacer tube 55. It will be seen that the two arms 46 and 47 are generally coplanar, as viewed from above, toward the rear of their pivot connection, they both bend toward the spacer tube 55 so that the forward ends of both arms, as viewed from above, are generally coplanar with the spacer tube 55.

FIGS. 30 and 31 illustrate a spacer 60. The spacer includes an enlarged head 70 and a shaft 71. The shaft is made of a bent resilient material having sufficient resiliency that when the shaft 71 is inserted into the end 56 of spacer tube 55, the resiliency of shaft 71 will cause it to be secured within the spacer tube 55. The spacer head 70 includes projections 72 and 73 on the top and bottom thereof, respectively. These engage dimpled recesses 74 and 75 in members 47B and 46B, respectively, in order to positively position the spacer head 70 and hence the spacer itself in position between the members 47B and 46B, when they are closed against the spacer.

Figure 32:
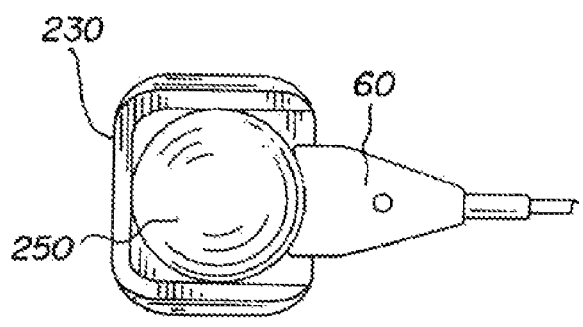
FIG. 32 is a plan view of the bottom part of an implant with the spacer positioned thereon.
Figure 33:
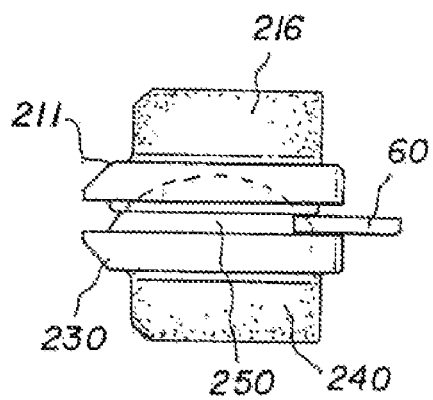
FIG. 33 is a side view of an implant with the spacer positioned therein.
Figure 33A:
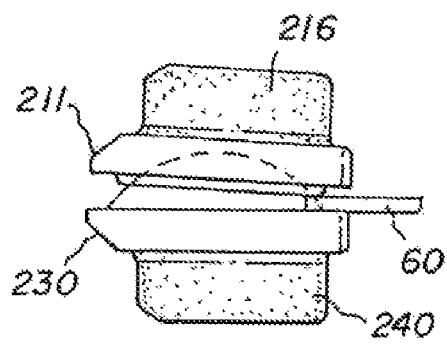
FIGS. 33A and 33B are side views similar to FIG. 33, but showing modifications.
Figure 33B:
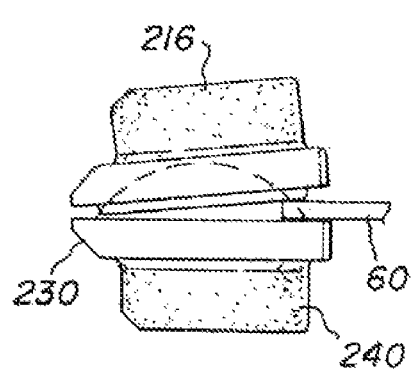

FIGS. 32 and 33 illustrate the position of the spacer 60 in its fully operative position wherein the arms 46 and 47 would be in their closed position securing the implant 210. In that position, the spacer 60 would rest on the very small ledge of the lower part just rearward of the plastic inlay 250 while the upper edge of spacer 60 would engage the bottom rearwardmost surface of the upper part, rearward of the raised rim 226, to thereby prevent the rear of the upper and lower parts from rotating about the plastic inlay 50 any closer to each other than permitted by the spacer 60. FIGS. 33A and 33B show how the spacer can be used to create anatomical angulation. In FIG. 33A, a thinner spacer 60 is used to create a kyphosis angle while in FIG. 33B a thicker spacer 60 is used to crease a lordosis angle.

Although the method of inserting an implant will be apparent from the preceding discussion of the instruments, there follows a brief summary of the method of the present invention.

Once the intervertebral space has been prepared and the cutouts C formed, the various insertion instruments may be used to insert the implant.

According to one insertion method, using the crossed linkage insertion instrument, the knob 4 is turned to move the arms 1 and 2 away from each other (actually moving the arm 1 upwardly away from the arm 2 which is fixed with respect to the body 3). The assembled implant is then placed between the arms 1 and 2, and more specifically, between the keel engaging portions 91A and 91B thereof, as described above, and the crossed linkage mechanism is closed. To close this mechanism, one simply pushes down on the thumb engaging portion of upper arm 1. This causes the arms of the crossed linkage to move freely to the right because the structure which engages the thread of the crossed linkage is such that it freely permits movement to the right, i.e., to the closing position, of the threaded rod. In one arrangement, this free movement to the right, to the closing position, is permitted because a beveled washer engages the threaded rod and prevents its free movement to the left, i.e., to the open position of the scissors linkage. In another arrangement, instead of a beveled washer, there is provided a conical nut which meets frictional resistance and thus causes threaded movement of the threaded rod to the left, to the open position, but moves to a friction free position to permit free movement of the threaded rod to the right upon downward pressure applied to the upper arm 1 to move the crossed linkage to the closed, implant engaging position. With the implant thus grasped by the insertion instrument, the implant is moved into the intervertebral space. The two arms 1 and 2 would then be moved apart in the manner described above, just enough to free the projections 93A and 93B from the indentations 221 and 243, after which the insertion instrument would be moved rearwardly out of the implant, leaving the implant in place.

Using the insertion instrument of FIGS. 19 22, one would move the thumb slide 35 to separate the arms 33 and 34 from each other. The implant would then be assembled onto the arms, as described above. Then, by moving the thumb slide in the other direction, i.e., to the left, as best shown in FIG. 22, a pin 36 which had been moved to the left to separate the arms 33 and 34, would then move to the right into a recess 39, thus permitting the arms 33 and 34 to move resiliently towards each other towards a closed position whereat the ends of these arms would hold an implant.

The method of operating the insertion instrument of FIG. 23 would differ slightly from the method of operating the insertion instrument of FIGS. 19 22. In the case of the insertion instrument of FIG. 23, there is no thumb slide, no recess 39 and no pin 36. To mount an implant on this insertion instrument, the operator would insert a slightly inclined implant, as shown in FIG. 23A, between the arms 33 and 34 to permit the ends of these arms to move into the keel recesses until the projections 93A and 93B reached and engaged the respective indentations 221 and 243. After the implant has been inserted, the insertion instrument of FIG. 23 would be removed by physically pulling the arms 33 and 34 out of the implant.

The method of operation of the insertion instrument shown in FIGS. 24 37 will be described below, especially with reference to FIGS. 34 37.

At the time that this insertion instrument is used, the correct size implant will have been determined by the use of trial implants. Referring to FIG. 34, the resilient shaft 71 of the correct size spacer 60 is inserted into the open end 56 of the tube 55 and moved all the way in until the collar 76 fits snuggly within the end of the tube 55, wherein the resilient bending of shaft 71 secures this spacer in place in the tube. Next, as shown in FIG. 35, the bottom part 230 of the implant is positioned on the arm 46, and specifically, on the forward narrow end 50 such that its projection 51 engages the recess 243 in the keel 240. At this time the forward end of spacer 60 is placed against the rear of the lower part as shown in FIG. 35, which position is also shown in FIG. 32. Next, the upper part 211 of the implant is placed onto the upper arm 47, and specifically the narrow front end 48 thereof such that the projection 49 engages the recess 221 in the keel 216. This might be done by a slight friction fit between these parts or, in the absence of a friction fit, one would simply hold the upper part 211 into position on this upper arm, which position is shown in FIG. 36, until the next step of closing the two arms together. Finally, as shown in FIG. 37, the forward ends of the arms 46 and 47, with the upper and lower implant parts mounted thereon, are brought together wherein the implant is held securely by these arms 46 and 47 and the spacer prevents the rear ends of the upper and lower parts from coming any closer together than permitted by the spacer 60 as shown in FIGS. 33 and 37. As noted above, a narrower or thicker spacer 60 may be used to create a kyphosis angle or a lordosis angle, respectively.

The insertion instrument is now moved to bring the implant 210 into the intervertebral space, with the keels 216 and 240 entering the cutouts C, as discussed with respect to earlier embodiments and as described with respect to FIGS. 5, 6, 8 and 9. During this final insertion position of this insertion instrument, the spacer 60 and its facing surfaces of members 46B and 47B are secured relative to each other by engagement of the projections 72 and 73 into recesses 74 and 75, respectively.

Once the implant is in place, removal of the insertion instrument is essentially the same as described above with respect to the other embodiments in that the arms 46 and 47 are separated slightly so that the projections 49 and 50 can move out of the recesses 221 and 243 while the top and bottom of the narrow ends 48 and 50, respectively, have not yet engaged the adjacent vertebral surface, whereupon the narrow ends 48 and 50 can be withdrawn out of the keels and the insertion instrument removed.

Although the invention has been described in considerable detail with respect to preferred embodiments thereof, it will be apparent that the invention is capable of numerous modifications and variations, apparent to those skilled in the art.

What is claimed:

1. An intervertebral implant assembly defining a leading end and an opposed trailing end, the intervertebral implant comprising:
    an upper implant part having an upper surface and an upper keel extending from the upper surface, the upper keel defining a first recess extending into an end thereof along a direction from the trailing end toward the leading end;
    a lower implant part having a lower surface and a lower keel extending from the lower surface, the lower keel defining a second recess extending into an end thereof along a direction from the trailing end toward the leading end; and
    an insertion instrument configured to engage the upper and lower implant parts for insertion of the upper and lower implant parts into an intervertebral space, the insertion instrument having opposed upper and lower arms that are moveable toward and away from each other, the upper arm configured to be received in the first recess and the lower arm configured to be received in the second recess.

2. The intervertebral implant assembly of claim 1, wherein the upper and lower arms are substantially parallel with respect to each other when engaged in the upper and lower keels, respectively.

3. The intervertebral implant assembly of claim 2, wherein the upper and lower arms are configured such that the upper and lower arms remain substantially parallel with respect to each other when moved toward and away from each other.

4. The intervertebral implant assembly of claim 3, wherein the upper and lower arms are operatively connected to each other with a crossed linkage.

5. The intervertebral implant assembly of claim 1, wherein the upper arm includes an upper projection and the lower arm includes a lower projection, the upper keel defines a first indentation and the lower keel defining a second indentation, the upper projection is configured to be received in the first indentation, and the lower projection is configured to be received in the second indentation.

6. The intervertebral implant assembly of claim 5, wherein the upper projection extends toward the lower arm and the lower projection extends toward the upper arm.

7. The intervertebral implant assembly of claim 6, wherein the first indentation is defined within the first recess, and the second indentation is defined within the second recess.

8. The intervertebral implant assembly of claim 1, wherein the upper implant part further has a lower inner surface opposite the upper surface, the lower implant part further has an upper inner surface opposite the lower surface, and the upper and lower implant parts are moveable with respect to each other along an interface defined by the lower and upper inner surfaces.

9. The intervertebral implant assembly of claim 8, wherein the lower inner surface defines at least one concave portion, the upper inner surface defines at least one convex portion configured to be received in the concave portion.

10. The intervertebral implant assembly of claim 9, wherein the interface is defined by the concave and convex portions.

11. The intervertebral implant assembly of claim 10, wherein the upper keel defines an upper surface and the upper keel is open at the upper surface, and the lower keel defines a lower surface and the lower keel is open at the lower surface of the lower keel.

12. The intervertebral implant assembly of claim 8, further comprising an insert configured to be disposed between the upper and lower implant parts.

13. The intervertebral implant assembly of claim 12, wherein when the insert is disposed between the upper and lower implant parts, the upper and lower implant parts are moveable with respect to each other about the insert.

14. The intervertebral implant assembly of claim 13, wherein the upper inner surface is defined by the insert.

15. The intervertebral implant assembly of claim 14, wherein the lower inner surface defines at least one concave portion, the upper inner surface defines at least one convex portion configured to be received in the concave portion, the interface defined by the concave and convex portions.

16. The intervertebral implant assembly of claim 15, wherein the upper keel defines an upper surface and the upper keel is open at the upper surface, and the lower keel defines a lower surface and the lower keel is open at the lower surface of the lower keel.

17. The intervertebral implant assembly of claim 12, wherein the upper keel defines an upper surface and the upper keel is open at the upper surface, and the lower keel defines a lower surface and the lower keel is open at the lower surface of the lower keel.

18. An implant insertion instrument comprising:
resilient upper and lower arms pivotally attached to each other, the upper arm having an upper implant engaging portion configured to be received in a first recess defined in an upper keel of an intervertebral implant and the lower arm having a lower implant engaging portion configured to be received in a second recess defined in a lower keel of the intervertebral implant, the upper and lower arms defining a gap therebetwen; and
a movable member at least partially disposed in the gap and moveable within the gap along a first direction and a second direction that is substantially opposite the first direction,
wherein movement of the movable member along the first direction causes the upper and lower implant engaging portions to angularly deflect toward each other and movement of the movable member along the second direction causes the upper and lower arms to angularly deflect away from each other.

19. The implant insertion instrument of claim 18, wherein the upper and lower arms further define a recess within the gap, the recess configured to receive the moveable member when the upper and lower arms are in respective implant holding positions.

20. The implant insertion instrument of claim 18, wherein the movable member comprises a thumb slide.

21. The implant insertion instrument of claim 20, wherein the moveable member further comprises a pin operatively coupled to the thumb slide, wherein movement of the thumb slide causes the pin to move within the gap.

22. The implant insertion instrument of claim 21, wherein the upper and lower arms further define a pin recess within the gap, the pin recess configured to receive the pin when the upper and lower arms are in respective implant holding positions.

23. The implant insertion instrument of claim 20, wherein the instrument body defines a sliding surface and the thumb slide defines an outer surface and an opposed inner surface that is configured to ride along the sliding surface.

24. The implant insertion instrument of claim 18, wherein the upper implant engaging portion comprises an upper projection that extends out toward the lower arm and the lower implant engaging portion comprises a lower projection that extends out toward the upper arm.

25. The implant insertion instrument of claim 18, wherein the upper and lower arms are monolithic with each other.

* * * * *